United States Patent
Klein et al.

(10) Patent No.: US 10,937,527 B2
(45) Date of Patent: Mar. 2, 2021

(54) IMMERSE SOFTWARE-AS-A-SERVICE PATIENT EMPOWERMENT PLATFORM FOR CLINICAL TRIAL PARTICIPANTS

(71) Applicant: Cytolon Digital Health AG, Berlin (DE)

(72) Inventors: Thomas Klein, Potsdam (DE); Matthieu-Patrick Schapranow, Berlin (DE); Ralf Schliehe-Diecks, Hoppegarten (DE)

(73) Assignee: BE THE PARTNER, INC., Medfield, MA (US)

( * ) Notice: Subject to any disclaimer, the term of this patent is extended or adjusted under 35 U.S.C. 154(b) by 171 days.

(21) Appl. No.: 15/129,829

(22) PCT Filed: Mar. 30, 2015

(86) PCT No.: PCT/EP2015/056894
§ 371 (c)(1),
(2) Date: Sep. 28, 2016

(87) PCT Pub. No.: WO2015/144931
PCT Pub. Date: Oct. 1, 2015

(65) Prior Publication Data
US 2017/0154166 A1    Jun. 1, 2017

(30) Foreign Application Priority Data

Mar. 28, 2014    (EP) ..................... 14162208

(51) Int. Cl.
*G16H 10/20*    (2018.01)
*G06Q 50/22*    (2018.01)
*G16H 10/60*    (2018.01)
*G06F 21/62*    (2013.01)

(52) U.S. Cl.
CPC ......... *G16H 10/20* (2018.01); *G06F 21/6245* (2013.01); *G06Q 50/22* (2013.01); *G16H 10/60* (2018.01)

(58) Field of Classification Search
CPC .............................. G16H 10/60; G16H 10/20
See application file for complete search history.

(56) References Cited

U.S. PATENT DOCUMENTS

| | | | |
|---|---|---|---|
| 2002/0016719 A1* | 2/2002 | Nemeth | G06Q 50/22 705/2 |
| 2003/0009367 A1* | 1/2003 | Morrison | G06F 19/326 705/7.33 |
| 2008/0114617 A1* | 5/2008 | Heniford | G06Q 50/22 705/2 |

(Continued)

FOREIGN PATENT DOCUMENTS

WO    WO-0217211 A2 *    2/2002    .......... G06F 19/324

OTHER PUBLICATIONS

EPO (European Patent Office, European Search Report issued in corresponding application EU 15 712 917.2 dated Nov. 15, 2019.

*Primary Examiner* — John P Go
(74) *Attorney, Agent, or Firm* — Joyce von Natzmer; Agris & von Natzmer LLP

(57) ABSTRACT

The invention relates to system and a computer implemented method for use in the course of a clinical trial and/or precision medicine, wherein patient metrics are acquired and the system comprises selected core modules, methods and/or automated services and selected empowerment apps.

20 Claims, 24 Drawing Sheets

(56) References Cited

U.S. PATENT DOCUMENTS

Figure 1:
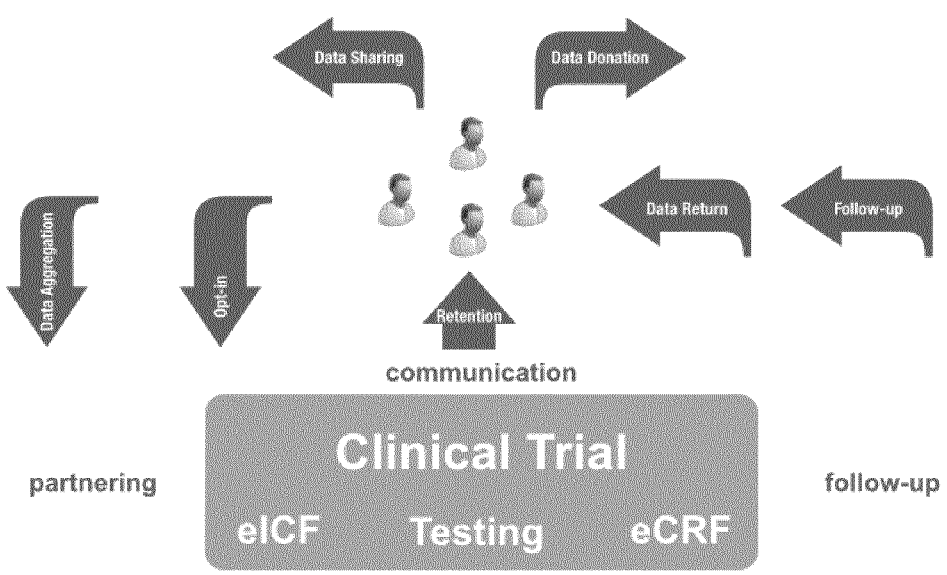

| | | | | |
|---|---|---|---|---|
| 2009/0307013 A1* | 12/2009 | Altounian | ............... | G06Q 30/06 |
| | | | | 705/4 |
| 2011/0307268 A1* | 12/2011 | Burdea | ................. | G06Q 50/22 |
| | | | | 705/2 |
| 2012/0004926 A1* | 1/2012 | Samar | ................... | G06F 19/328 |
| | | | | 705/2 |
| 2012/0089418 A1* | 4/2012 | Kamath | ................ | G06Q 50/24 |
| | | | | 705/3 |
| 2012/0310670 A1* | 12/2012 | Pruitt | .................... | G06Q 10/10 |
| | | | | 705/3 |
| 2013/0017807 A1 | 1/2013 | Rooyen et al. | | |
| 2013/0145479 A1* | 6/2013 | Naveed | ................. | G06F 21/62 |
| | | | | 726/27 |
| 2013/0218594 A1* | 8/2013 | Skocic | .................. | G06Q 10/10 |
| | | | | 705/3 |
| 2013/0304504 A1* | 11/2013 | Powell | .................. | G06Q 10/06 |
| | | | | 705/3 |

* cited by examiner

Figure 14

Figure 23

IMMERSE SOFTWARE-AS-A-SERVICE PATIENT EMPOWERMENT PLATFORM FOR CLINICAL TRIAL PARTICIPANTS

CROSS-REFERENCE TO RELATED APPLICATIONS

This is the U.S. national stage of International application PCT/EP/2015/056894, filed 2015 Mar. 30 designating the United States and claiming priority to European Patent application EP14162208.4, filed 2014 Mar. 28.

BACKGROUND

Patients participating in clinical trials nowadays are de-identified subjects of research for the pharmaceutical industry. The existing unidirectional relation suffers from various downsides, e.g. missing transparency, communication, and no partnering.

The Guidelines for Good Clinical Practice (GCP) introduced by the International Conference on Harmonisation (ICH) define the foundation for implementing clinical trials involving human subjects, which are mostly 1:1 implemented in individual countries, e.g. United States of America (USA) and European Union (EU) [1]. In addition to processes in the course of the clinical trial, they define requirements for created document artifacts, e.g. Informed Consent Form (ICF) or Case Report Form (CRF), and the interaction between involved actors, e.g. investigators, sponsors, and trial participants. These guidelines aim to support the generation of reproducible clinical trial data representative for a specific population cohort.

Today, sponsors and clinical trial participants are not able to build on bidirectional communication during the course or after the end of an active clinical trial. On the one hand, trial participants are considered as subjects of research without the chance to provide direct feedback. In consequence, clinical trial participants lack an overall transparency of the clinical trial they participate in. On the other hand, trial sponsors are interested in keeping patients engaged during the complete course of the clinical trial, e.g. to keep the dropout rate metric low. Legal monitoring organizations, such as Food and Drug Administration in the USA or European Medicines Agency (EMA) in Europe, monitor running clinical trials constantly and might stop them prematurely, e.g. when dropout rates exceed a certain threshold as it might result in biased statistical results [2].

Today the pharmaceutical industry is facing serious difficulties in recruiting patients for clinical trials. This is due in part to the fact that the industry does not have direct or indirect access to potential candidates. Also selected candidates who would be suitable for a clinical trial but due to individual features cannot be included in the trial, are lost and are not available for a further phase of the trial, marketing or a newly created trial project.

It is necessary to be able to return generated data to the user or patient and to have the opportunity to contact the user or patient, so that he or she remains in the study or trial or participates in another trial later or is informed about new products as a consumer.

The pharmaceutical industry has the need to know the early or first users of their products and to be able to stay in contact over the long term, without violating regulatory guidelines. This requires the development of completely new tools for the marketing of products with the help of a system and the associated data.

Currently, the market for health-related software products is emerging, e.g. Microsoft HealthVault and Apple Research Kit [19], [20]. As a result, human-readable userfacing apps are important to turn patients as subjects of research into informed partners of healthcare experts. The standardized access and exchange of healthcare related data is equally important as an integrated ecosystem, which offers integration of the variety of apps and services in an easy way.

DESCRIPTION OF THE INVENTION

The technical problem underlying the present invention is to provide an improved or alternative system or a computer implemented method for use in the course of a clinical trial and/or precision medicine.

The object is attained by means of the independent claims. Advantageous embodiments are disclosed by the dependent claims.

In a first embodiment the invention relates to a system for use in the course of a clinical trial and/or precision medicine, said system comprising
a software platform, wherein users can create a user profile and can communicate with each other,
a storage unit, said storage unit comprising application data and user data,
a processor, wherein said processor analyzes application data and/or user data forming a longitudinal database,
wherein the system acquires metrics, which are documented as data points in the longitudinal database storage accessible by users, and
wherein the system comprises core modules selected from the group comprising personal health record module, messaging module, newsletter module, search module, blogging and discussion forums module, calendar module, notes module, application store and ecosystem module, location-based services module, rating module, payment services module, data exploration and analytics module, and
wherein the system provides methods and/or automated services, selected from the group comprising retention service, rewards and incentive service, patient education service, reminder service, medication adherence and compliance service, self-reported outcomes, surveys and questionnaires service, community and social network service, reimbursement service, campaign service and/or NB testing and
wherein the system comprises empowerment apps, which build on platform services and/or functions.

In the given invention, we present a Patient Empowerment Platform—a unique SaaS platform for patients within and outside of clinical trials. The platform of the invention provides an immerse software system in the course of a clinical trial and precision medicine. As a result, the system of the invention acts as trusted intermediate for all involved parties, such as patients, investigators, and pharmaceutical sponsors. Therefore important components of the system are core modules, methods/services and empowerment apps. Core modules also referred to as core apps are provided as an integral component of the platform to have a common set of functionality available. It is preferred that empowerment apps can influence metrics.

The invention introduces a Patient Empowerment Platform, an immerse software system enabling empowerment of clinical trial participants during and after the participation within clinical trials. The invention's approaches contributes to improve clinical trials in all of their phases, e.g. during the design and the screening of patients, which consumes as of today a significant amount of the overall clinical trial time [3].

The platform of the invention transforms patients as subjects of research into partners of clinical development and places the patient in the heart of the clinical development: a demanding challenge for which the pharmaceutical industry currently has no clear solution. Continuous engagement in the form of a constant dialogue with patients, their caregivers or their advocacy organization as partners, is missing as of today.

The invention provides a secure online software platform for users involved in clinical trials. The users interacting with the platform are patients, investigators, physicians, sponsors and/or their representatives, e.g. Clinical Research Associates (CRAs). The platform offers the next level of data aggregation and data exchange services between pharmaceutical sponsor conducting clinical trials and patients participating in them. A pivotal service is the return of personal data to participants of clinical trials. This is the quid pro quo to turn subjects of research into partners of the pharmaceutical industry. This interplay of data return with other digital patient-oriented clinical development services with their data and their care givers will drive the future of patients as partners in research and development improving the patient experience.

The system of the invention improves patient engagement throughout a clinical trial and therefore satisfies of a long-felt need among experts.

The term "patient engagement" refers preferred to the communication with patients and the use of online patient tools. Several factors are relevant for an extensive patient engagement. The factors include but are not limited to knowledge, skill, ability, willingness of patients to manage their health and collaboration between patients and investigators to design, manage and achieve health outcomes.

In a preferred embodiment the users interacting with the platform are selected from the group comprising patients, patient advocacy group members, investigators, physicians, sponsors and/or their representatives, preferred Clinical Research Associates (CRAs), and/or researchers.

The system of the invention enables direct communication between all involved users also referred to as actors while keeping the privacy of individual parties protected, e.g. trial participants remain de-identified.

It is further preferred that the system is not only used during the course of a clinical trial but also afterwards. This represents a major advantage in comparison with the state of the art and offers lots of opportunities for further in the area of precision medicine, patient empowerment and/or patient engagement.

I. For Patients

Patients are empowered by the system to better control their participation in the clinical trial. For example, patients are enabled to communicate with all involved trial parties without losing their de-identification and the platform host acts as trusted intermediate to acquire their personal clinical data in a human-readable format from the sponsor after providing their personal opt-in. This is an important advantage compared to the state of the art.

The system acts as an incubator for a real patient empowerment building on patient's reviewed trial data and as a provider of an ecosystem of related services and products even beyond the course of the clinical trial. Thus, the platform of the invention provides a secure and controlled online setting enabling (a) a new level of transparency and trust between clinical trial patients and the pharmaceutical industry, (b) patient empowerment with biomedical innovation enabling more accurate and well-controlled delivery of medication, and (c) improved patient health over the long term due to the increased use of clinical trial data. By building a community of highly motivated and engaged users, the foundation for numerous future and innovative services are formed.

II. For Investigators

Investigators are essential actors in the communication with other users of the platform as they are the first point of contact for the patients. Thus, the system integrates them in all selected activities between sponsors and patients, i.e. investigators are always kept up-to-date when communication with their patients occurs. In selected processes, such as data return as described below, investigators are required to review, annotate, or release data to patients, e.g. to confirm that they match their individual notes. As a result, the platform of the invention leverages a unique level of transparency to investigators.

III. For Sponsors

The new system enables pharmaceutical companies seamlessly to (a) establish contact with a patient at the beginning of a trial, (b) maintain the contact during the trial, thus increasing the likelihood that the patient completes the trial, and (c) continue to keep in contact with patients even after the end of a trial. The system integrates also involved investigators in this process, e.g. they can review personalized clinical trial data prior to its release to patients or they can directly react to patient-reported outcomes. With the invention a longitudinal database of highly engaged and empowered participants or alumni of clinical trials is established for the first time, which can be used for further innovative new services, e.g. research purposes.

It is an advantage of the invention that a bi-directional communication between industry and clinical trial patients participants is enabled during and after the clinical trial, whereby the anonymity of the users is preserved.

IV. Patient Empowerment Metrics

It is preferred that patient empowerment metrics are used for measurement and/or evaluation of patient's empowerment on the platform, during patient's participation in clinical programs, trials, and/or activities. These metrics are important criteria for the assessment and analysis of a patient's empowerment and therefore valuable data for investigators and/or sponsors.

In the following, we outline preferred patient empowerment metrics:

Preferred patient empowerment metrics are selected from the group comprising personal performance, quality of life, social interactions, disease, program knowledge, customer experience, medication adherence and compliance.

These selected metrics are used to measure individual patient empowerment. Based on these metrics, the software system architecture of our platform was designed. It provides an environment to deploy and run disease-specific tools and apps to measure patient metrics and directly react to changes in these metrics. As a result, the invention provides a set of patient empowerment apps and how they support our patient empowerment processes.

A. Personal Performance

The personal performance metric is in an indicator for how well a user performs compared to a set of similar users. For that, a set of measurable factors needs to be acquired by the user on regular basis, e.g. using self-reported outcomes or surveys. Amongst others, the parameters can be used to compare the personal performance with a cohort of similar users:

Number of users with the same disease on the platform

Number of users already clinical trials

Next steps in the course of users personal treatment according to users plan

Users donated data was used to help two other patients this week

Regular statistics like "your donated data was used to help two other patients this week" help to encourage patients, which is an advantage of the invention.

B. Quality of Life

The quality of life metric combines selected attributes to characterize the user's ability to live a high-quality life. With the help of these attributes it is possible to derive changes of medical scores, e.g. Eastern Cooperative Oncology Group (ECOG) or Karnofsky, and to initiate immediate reactions [5]. These attributes can be acquired explicitly by self-reported outcomes or by analysis of changes in behavior, e.g. changes in medication adherence or missed appointments. Amongst others, the following question can be used to acquire relevant attributes:

Questions:

"Identify three common enjoyable activities", e.g. fishing, visiting family members "Have you done any enjoyable activity within the last three days?"

"Have you been able to leave the house in the recent days?"

"How well are you able to move around on a school grade scale?"

"When was the last time you were able to participate in an enjoyable hobby?"

C. Social Interactions

The metric for social interactions is important to assess whether the user are able to interact. This can be done by acquiring self-reported outcomes or to derive by their change in participation in virtual communities or campaigns. Amongst others, the following questions can be used to acquire relevant attributes:

"Have you talked to anyone else about your treatment or conditions?"

"Do you use any kind of social media to exchange, if yes which?"

"Do you visit any patient groups?"

By providing adequate educational measures or near patient groups or doctors to talk to this metric can be influenced.

D. Disease/Program Knowledge

The user's understanding of her/his disease and the awareness of next steps in the program are essential to increase user's attractions. As a result, users are able to access educational materials in alternative ways.

E. Customer Experience

Customer satisfaction and customer experience are evaluated after the participation in a certain module, program, or trial of the platform. This metric is acquired by specific surveys and questionnaires, which are sent to users after the end of the participation. We consider online surveys as an integrated component for directed feedback. As a result, users receive an invitation to participate in the survey via their Inbox as described above. If the user is not answering the survey within a certain period of time, additional engagement techniques, such as reminders or incentives can be applied to improve response rate.

F. Medication Adherence and Compliance

Medication compliance is especially important for the participation in trials and medical programs. These information are acquired to understand whether the applied the patient is responding or not, e.g. in terms of medication, dosage, or its combination. For example, elderly people often fail to comply with prescribed schemas or dosages, e.g. due to the variety of pills to take, missing active reminders, or mental diseases [6]. The system acquires this metric as part of the user-reported outcomes, which are documented as longitudinal data in the user profile on the platform. The survey techniques are incorporated to log the required data.

V. Patient Empowerment Methods/Methods and/or Automated Services Provided by the System For patient empowerment, the following categories of communications are defined:

Unidirectional (exchange of information, no evaluation needed)

A: Triggered by patient, e.g. update appointment

B: Triggered by site, e.g. monthly newsletter

Bi-directional (requires evaluation of responses and adequate reaction):

C: Triggered by patient, e.g. self-reported outcomes

D: Triggered by site, e.g. customer experience survey

TABLE I

Tab. I provides a mapping of patient empowerment method and selected platform apps that are incorporated to implement these processes.

| App/ Method | Patient Retention | Gamification | Rewards, Incentive System | Patient Education | Reminders | Medication Adherence, Compliance | Self-reported Outcomes, Surveys, Questionnaires | Community, Social Network | Reimbursement | Campaigns | A:B Testing |
|---|---|---|---|---|---|---|---|---|---|---|---|
| Opt-In | ✓ |  | ✓ |  |  |  |  |  |  |  |  |
| Data Return | ✓ | ✓ |  | ✓ |  | ✓ |  |  |  |  |  |
| Data Sharing | ✓ | ✓ |  |  |  | ✓ |  |  |  |  |  |
| Data Donation |  |  | ✓ |  |  |  |  |  |  |  |  |
| Inbox | ✓ | ✓ |  | ✓ | ✓ | ✓ | ✓ | ✓ | ✓ | ✓ | ✓ |
| Tasks | ✓ | ✓ |  |  | ✓ | ✓ | ✓ |  | ✓ | ✓ |  |
| Medication history | ✓ | ✓ |  | ✓ | ✓ | ✓ |  | ✓ | ✓ |  | ✓ |
| Pharma., Medication Alerts | ✓ | ✓ |  |  | ✓ | ✓ | ✓ |  |  |  |  |

TABLE I-continued

Tab. I provides a mapping of patient empowerment method and selected platform apps that are incorporated to implement these processes.

| App/Method | Patient Retention | Gamification | Rewards, Incentive System | Patient Education | Reminders | Medication Adherence, Compliance | Self-reported Outcomes, Surveys, Questionnaires | Community, Social Network | Reimbursement | Campaigns | A:B Testing |
|---|---|---|---|---|---|---|---|---|---|---|---|
| Investigators, Doctors | ✓ | ✓ | ✓ | ✓ |  |  |  | ✓ | ✓ |  |  |
| Community, Social Network | ✓ | ✓ |  | ✓ |  |  | ✓ | ✓ |  | ✓ | ✓ |
| Disease and Treatment Knowledge Base | ✓ |  | ✓ | ✓ |  | ✓ |  | ✓ | ✓ |  |  |
| Personal Performance Dashboard | ✓ | ✓ | ✓ | ✓ |  |  | ✓ | ✓ |  | ✓ | ✓ |
| PHR | ✓ | ✓ | ✓ | ✓ |  | ✓ |  |  |  | ✓ | ✓ |
| Messaging | ✓ | ✓ | ✓ | ✓ | ✓ | ✓ | ✓ | ✓ | ✓ | ✓ | ✓ |
| Newsletter | ✓ | ✓ | ✓ | ✓ | ✓ | ✓ | ✓ | ✓ | ✓ | ✓ | ✓ |
| Search |  |  | ✓ | ✓ |  |  |  |  |  |  |  |
| Blogging, Discussion Forums | ✓ | ✓ | ✓ | ✓ |  |  | ✓ |  |  | ✓ | ✓ |
| Calendar | ✓ | ✓ | ✓ |  | ✓ | ✓ | ✓ |  | ✓ |  | ✓ |
| Notes | ✓ |  | ✓ | ✓ |  |  |  |  |  | ✓ |  |
| App Store, Ecosystem | ✓ | ✓ | ✓ | ✓ |  |  |  |  | ✓ |  |  |
| Location Services | ✓ | ✓ | ✓ | ✓ | ✓ |  | ✓ |  |  | ✓ | ✓ |
| Rating | ✓ | ✓ | ✓ |  |  |  | ✓ | ✓ |  | ✓ |  |
| Payment Services | ✓ | ✓ | ✓ |  |  |  | ✓ |  | ✓ |  |  |
| Data Exploration, Analytics | ✓ | ✓ |  | ✓ |  |  | ✓ |  |  | ✓ |  |

In the following, we share details about selected incorporated methods for empowerment of users of the platform.

A. Patient Retention

Figure 4:
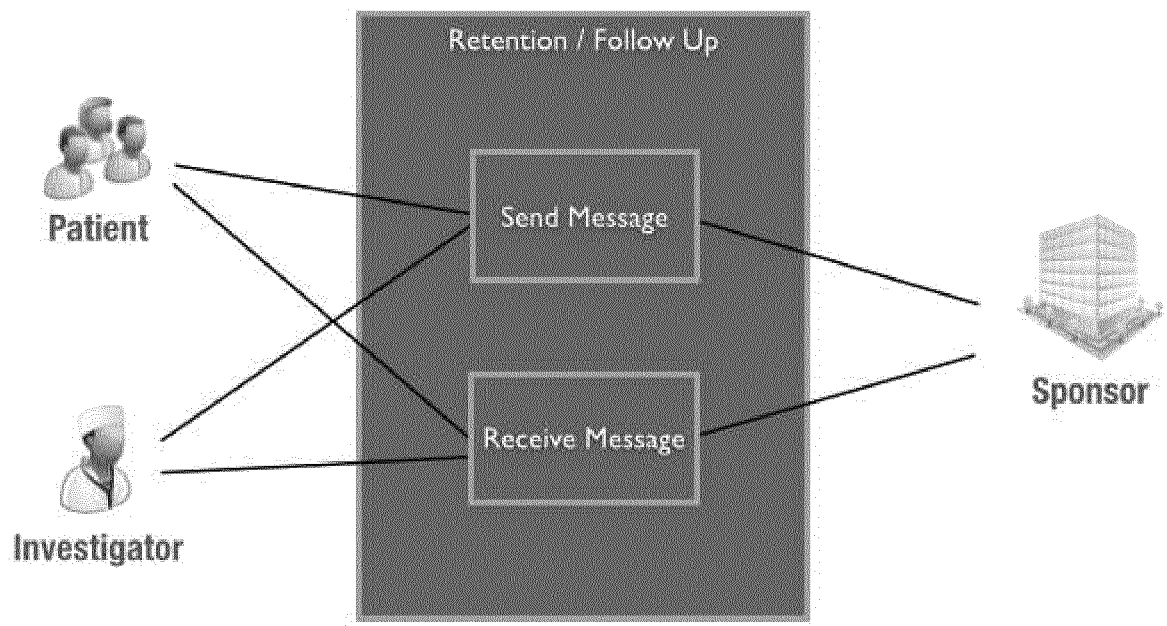

FIG. 4 summarized the following use cases of the Data Return process:

The Sponsor shall be able to provide CRF data and CSR Lay Summaries and inform on data availability via the system, and Patient and investigator shall be informed on data availability and be able to view and download the returned data via the system.

Figure 6:
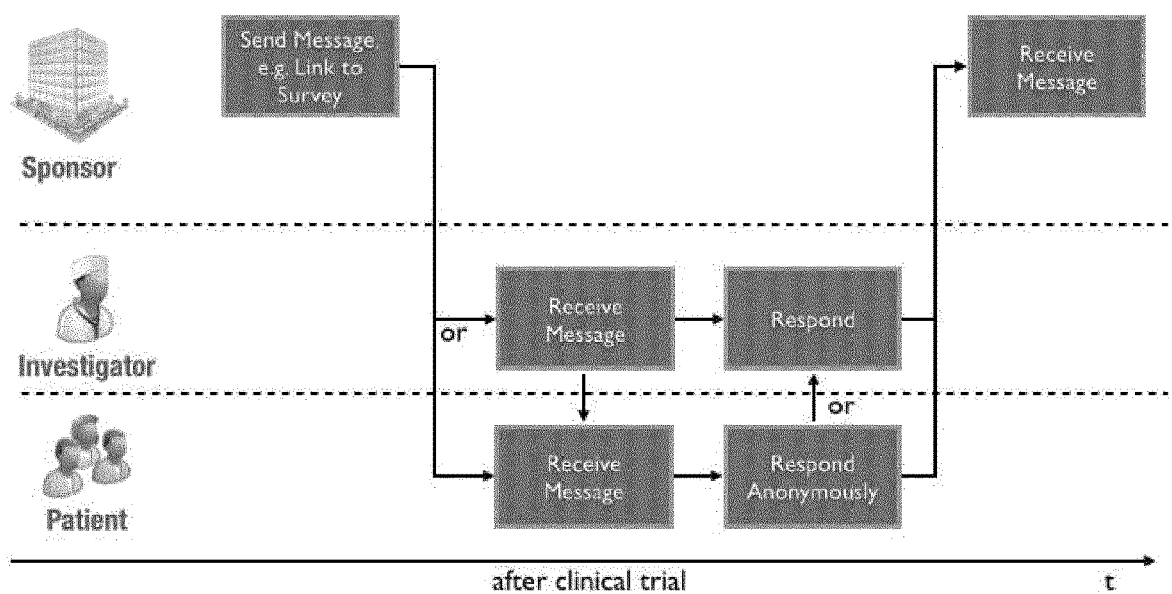

FIG. 6 shows the main steps of the retention process involving the user types "Sponsor", "Investigator" and "Patient". The sponsor can create messages in the system and send them to investigators and patients on a per trial basis or to single users. Investigators and patients are then able to receive these messages within the system and are optionally informed on new messages via email. Principally the system of the invention (also called Health Engine) allows bi-directional communication if desired. First time a real-time dialogue between industry and clinical trial patients is possible during and after the study—while preserving the anonymity. Publications show that this communication can have a critical impact on the success of the trial.

B. Gamification

It is preferred that the system comprises a gamification method, wherein gamification is the application of game playing elements and activities to trial-related activities.

We refer to Gamification as the application of game playing elements and activities to other areas of activity [7]. In particular, we apply these techniques to improve patient empowerment during the course of a clinical trial and the participation on the platform.

We define a virtual currency, Cytolon Health Points (CHP), which can be acquired by user of the Cytolon platform by performing different activities. The individual amount of CHP can be used to compare individual performance on the platform with other participants.

When reaching certain thresholds, the user enters a next level providing additional functionality or services around the personal health targets.

Preferred activities in the context of gamification, which result in release of CHP to the user, are amongst others:

Pills taken as indicated,

Doctor visits as scheduled,

Positive lab results, e.g. all blood results are within normal thresholds,

Personal daily targets reached, e.g. sport activities performed, logged in for certain education material, or survey answered, and Participation in campaigns, e.g. completing four succeeding doctor visit result in a one-time bonus of twice the amount of CHP.

C. Rewards and Incentive System

We introduce a rewards system for end users of the platform. As a result, user of the platform can transform their obtained CHP into real assets. For that, we follow Robinson et al. and define the following categories of incentives [8]:

Non-financial incentives, e.g. Badges once personal goals reached, coffee mugs, pens, magnets, buttons, pins, etc., and Financial incentives, e.g. Pharmacy gift cards, free annual physical examination, voucher for personal education, etc.

D. Patient Education

As a user suffering from a certain disease, the knowledge about the disease is important. As a result, links to educational material, e.g. reviewed websites prepared for non-medical experts, books, or selected publications, are beneficial to improve personal education. If the user has questions with respect to the disease personal interviews with medical experts or connections to find patient groups are considered as helpful as well.

E. Reminders

Figure 24:
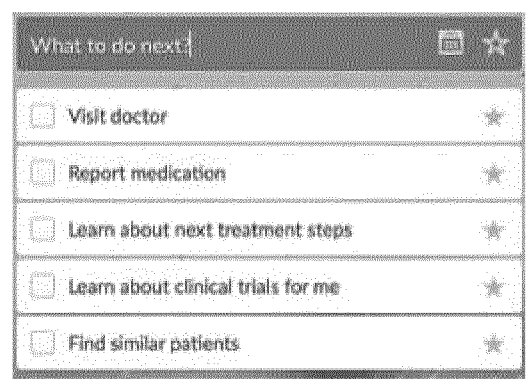

It is preferred that the invention makes use of regular reminders to improve active participation rate of participants as depicted in FIG. 24. Users of the platform see their personal reminders in the calendar and the task list app. In addition, they can configure push notification services in their profile preferences, e.g. text messages sent to their cellular phones or e-mails sent to their mailboxes.

Users can setup—amongst others—the following reminders to send out notifications for:

Scheduled or updated appointments, notifications are sent out at least 24 hours before the appointment, The regular intake of prescribed medication, Request new medication package based on prescription plan, Document symptoms in online diary, Document personal quality of life performance, Complete surveys to receive incentives, and Perform certain actions to reach for personal daily goal.

F. Medication Adherence and Compliance

A preferred method and/or automated service of the invention is the medication adherence and compliance method. It is preferred that the platform of the invention forms a longitudinal database of self-reported outcomes, preferred medication intakes and/or possible side effects by combining data about latest information about user's current medication, user's medication history, related information preferred documented side effects and/or intake plan with surveys and/or documentation of self-reported outcomes provided by patients on a regular basis.

Logging personal medication history is valuable for all involved actors of the platform. Users have a single source of information, where they find latest information about their current medication, the medication history, and related information, such as documented side effects or intake plan. Combined with surveys and documentation of self-reported outcomes, the platform forms a longitudinal database of self-reported medication intakes and possible side effects. The latter provides the complete medication history to investigators to get an overview about existing medication intake, possible side effects, and the user's medication adherence.

G. Self-Reported Outcomes, Surveys and Questionnaires

The use of online or paper-based surveys and questionnaires is an established way to acquire user feedback, e.g. self-reported outcomes [9]. On the platform, we incorporate surveys as follows:

Selection of predefined, disease-specific surveys,

Definition of user-defined surveys, and

Assignment to individual users or users groups.

Acquired results can be explored using integrated data analysis tools.

H. Community and Social Network

The virtual interaction between individuals is as important as their physical interactions. As a result, the invention provides functionality for finding of users, e.g. with similar chronic diseases, in the same area, visiting the same sites, etc. As a result, it offers the flexibility to build virtual relationships, e.g. friendships, and to share experiences, notes, messages, or knowledge.

I. Reimbursement

Selected activities that are correlated with the participation in the trial can be nominated for reimbursement. The reimbursement is considered as a financial incentive, which enables user to perform a certain action, which they would not be able to perform otherwise. Examples for are reimbursement of hours of childcare during doctor visits, vouchers for taxi rides limited to a maximum rate, or discounts on selected pharmacy products. The use of reimbursement is only reasonable for selected trials and users. As a result, reimbursement is not a generic patient retention method, but it is preferable to apply to users that show a high or rising probability of dropout to keep them engaged. However, this method needs to be used carefully and potentially as a one-time benefit otherwise it could be expected by time user as a default benefit.

J. Campaigns

We incorporate campaigns on the platform as a strong trigger to increase patient empowerment for selected patient groups. Amongst others, the following campaigns are used on the platform:

Complete four doctor visits, you qualify for twice the amount of CHP,

Sign up for regular reminders to improve visit rate results in the Cytolon Active Empowerment Badge, Access educational material about your indication or disease to obtain disease-specific knowledge and learn more about next steps in your treatment and successfully complete a survey results in the Cytolon Disease Expert Badge, Use Cytolon's Data Return Service (DRS) to keep track of your personal healthcare data results in 500 CHPs, and Track your per personal performance by adding Self-Reported Outcomes (SRO), e.g. how do you feel today?

K. A:B Testing

The platform provides the technical foundation to gather new scientific insights by providing cohort data analysis features to drive evidence-based medicine. Researchers of the sponsor can separate users into randomized cohorts to apply A:B testing to them [10]. Thus, they can validate their hypotheses and to directly measure impact of taken actions. For example, we use NB testing to constantly evaluate the impact of incorporated patient empowerment techniques in the course of clinical trials and provide metrics as a monthly report to sponsors.

VI. Software System Architecture

In the following, the software system architecture of a preferred platform of the invention is outlined.

Figure 7:
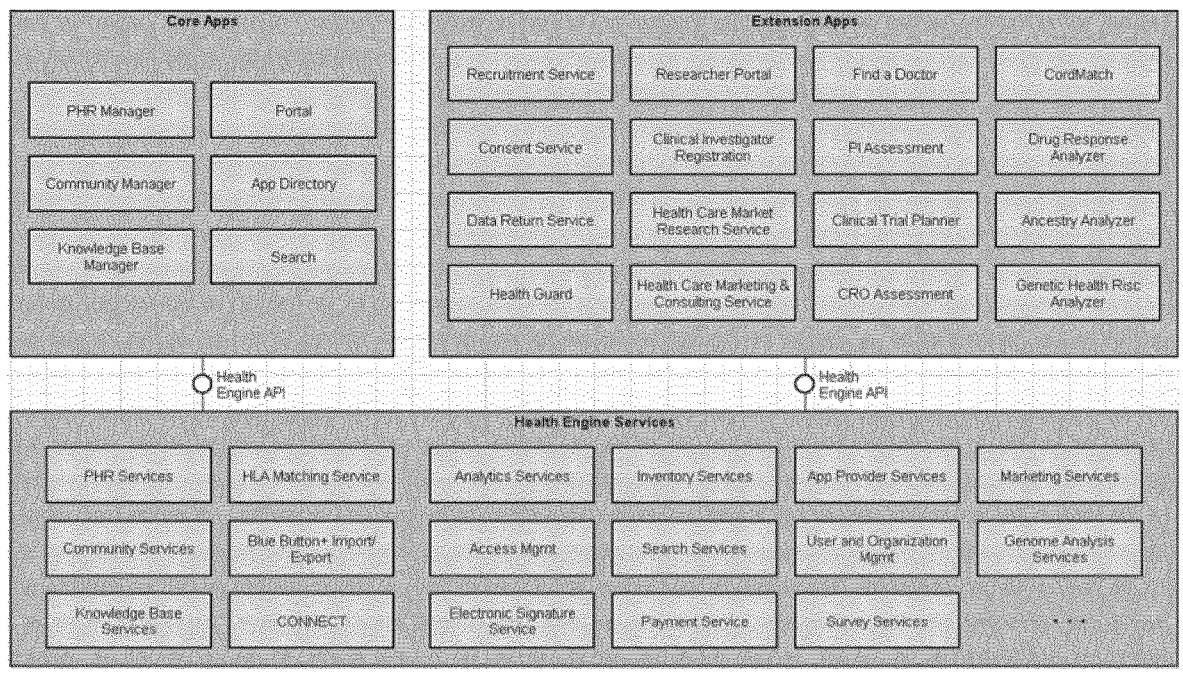

FIG. 7 depicts the schematic interaction of a preferred platform services and empowerment apps A. Users and Access Rights It is preferred that the platform implements access rights management using Rule- (RuBAC) and Role-Based Access Control (RBAC) and Single-Sign on (SSO) Functionality and Methods for Authentication.

Figure 8:
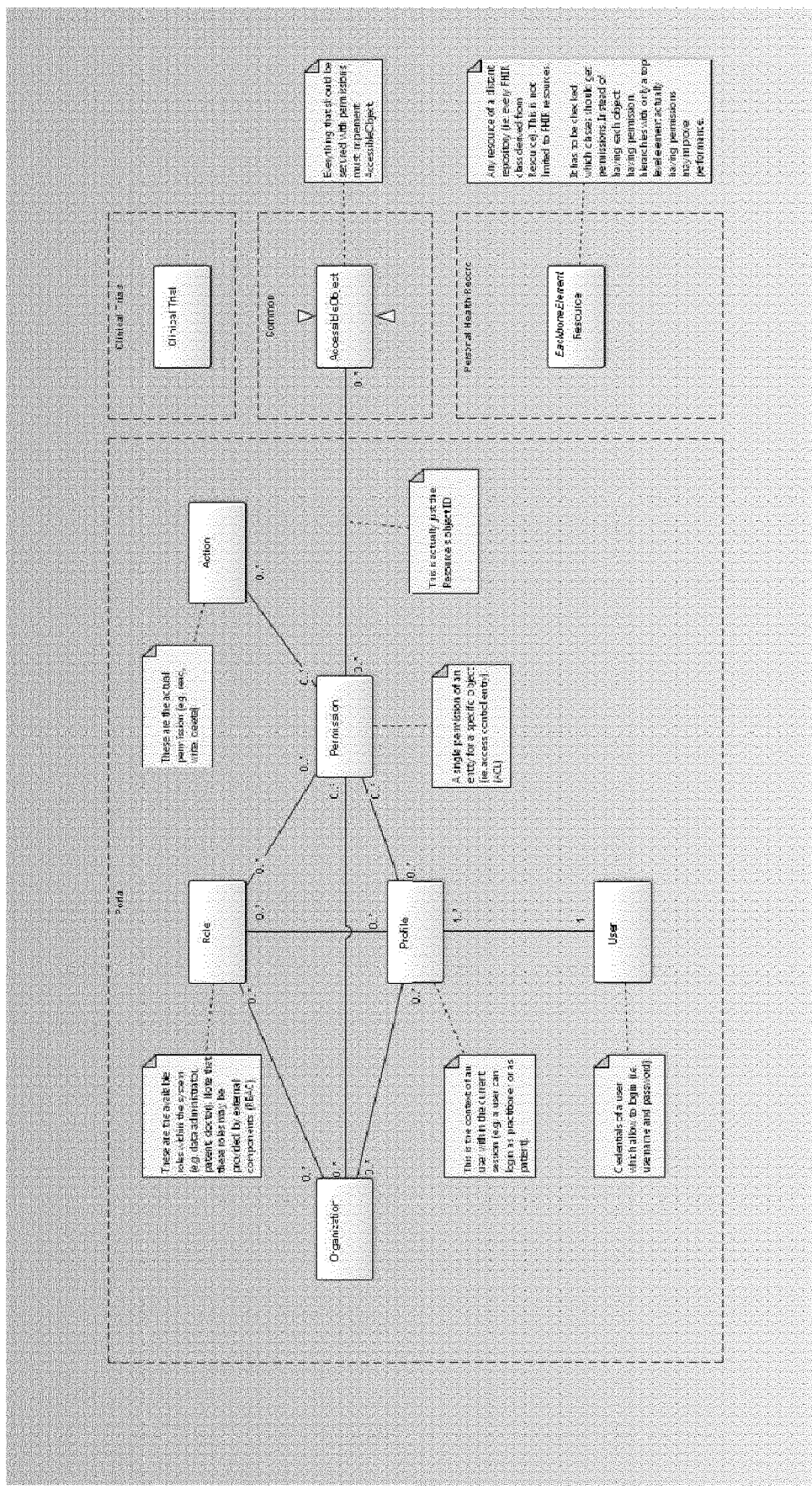

The platform implements latest access rights management using Role-Based Access Control (RBAC) as depicted in FIG. 8. Furthermore, the platform implements Single-Sign On (SSO) functionality, which enables the user to access apps and functions requiring authentication by providing their personal credentials only once. Furthermore, the platform implements latest techniques for authentication, e.g. password, OAuth2, or X.509 certificates [12], [13].

Fine-grained resources, e.g. business objects, such as a single lab result, individual records, or attributes, can be defined. Access rights, such as the operations Create, Read, Update, Delete (CRUD), are managed on resource-level. Individual access rights are assigned to user roles, organizations, or profiles, while individual users are assigned to one of multiple of the latter. Thus, users, user roles, and associated organizations of the platform are maintained. A user can be assigned to multiple organizations whilst organizations can have multiple user roles. Access rights for individual apps and software models of the platform are managed via user roles abstracting from individual users.

It is preferred that entities are selected from the group comprising resources, permissions, roles, organizations, user groups, user and/or profile are defined in the platform's security roles concept.

Figure 9:
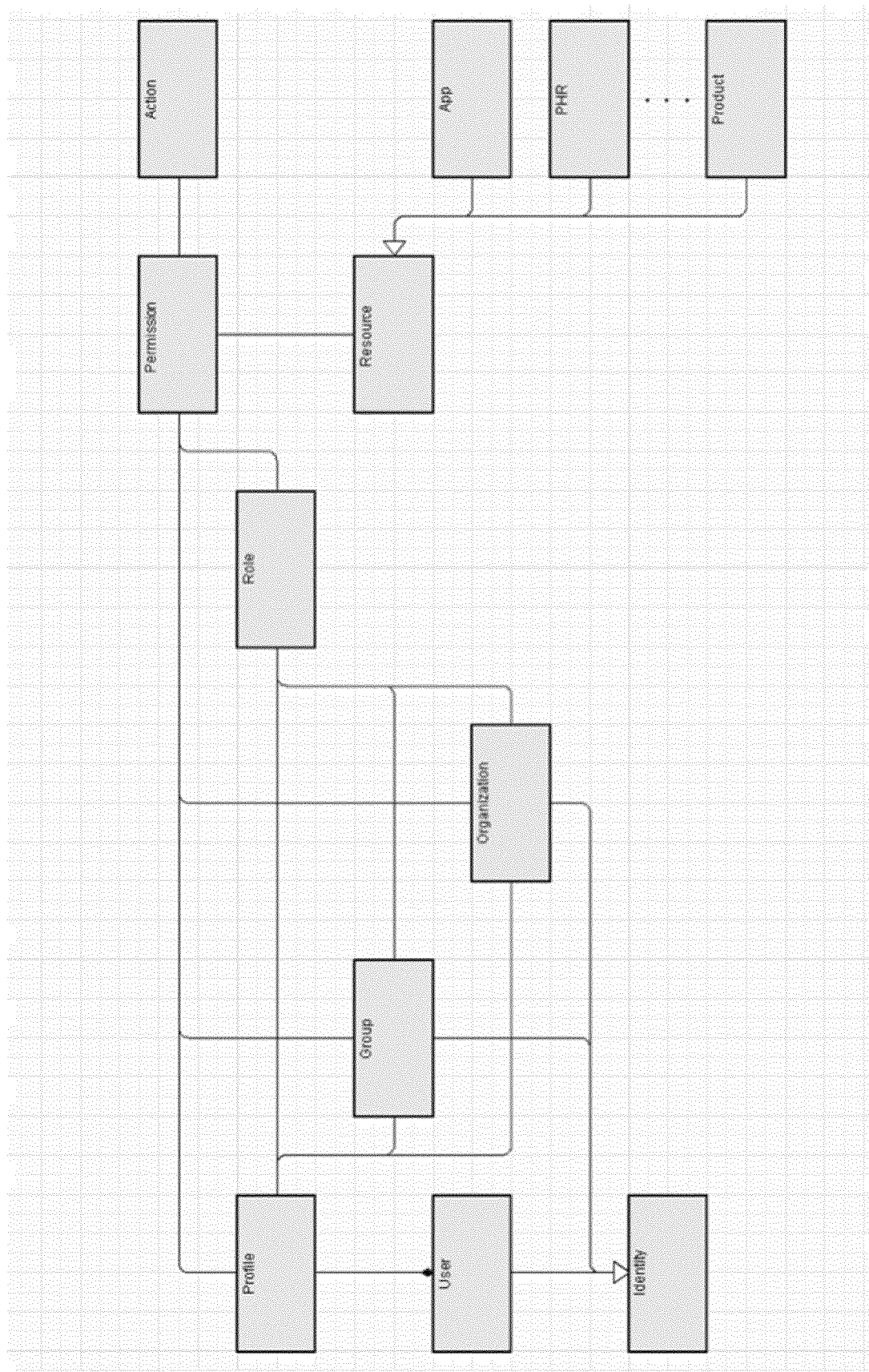

The following entities are defined in the platform roles concept whilst their interaction is depicted in FIG. 9:
- Resources describe a specific object within the platform, e.g. apps, products, blog, forum or discussion messages, etc. An operation can be performed on selected resource only if the user holds the required access rights on the given resource.
- Permissions are assigned to individual resources, which allows individual operations, e.g. CRUD, on these resources. Permissions can be assigned to roles, profiles, user groups, and organizations. Permissions are cumulative.
- Roles group permissions on specific system resources, which are functionally assigned. Roles can be assigned to profiles, user groups, or organizations whilst permissions are cumulative.
- Organizations can have multiple profiles and/or roles assigned. Organization can be hierarchically structured and inherit access rights.
- User Groups combine multiple user roles and/or individual permissions. User roles can be hierarchically combined, i.e. they may inherit permissions and/or user roles.
- User is assigned to at least one profile, which maps all connections to more fine-grained entities. Users may be assigned to multiple user groups.
- Profile provides the user context; thus changing the profile will result in a change user context, e.g. apps or functionality, without creating a new user.

The management of access rights on the platform abstracts from individual users, which makes it easier to control access for a high number of users without granting them individual access rights. However, it is still possible to assign access rights directly to individual users without the indirection of user roles, which allows customizing access rights on per user basis.

Individual apps on the platform define required user roles, e.g. to provide a multi-modal user interface or to allow subscription to the app. If the current user lacks these mandatory user roles, she or he is neither able to see a certain app on the app store nor is able to subscribe to it.

B. Data Model

Figure 10:
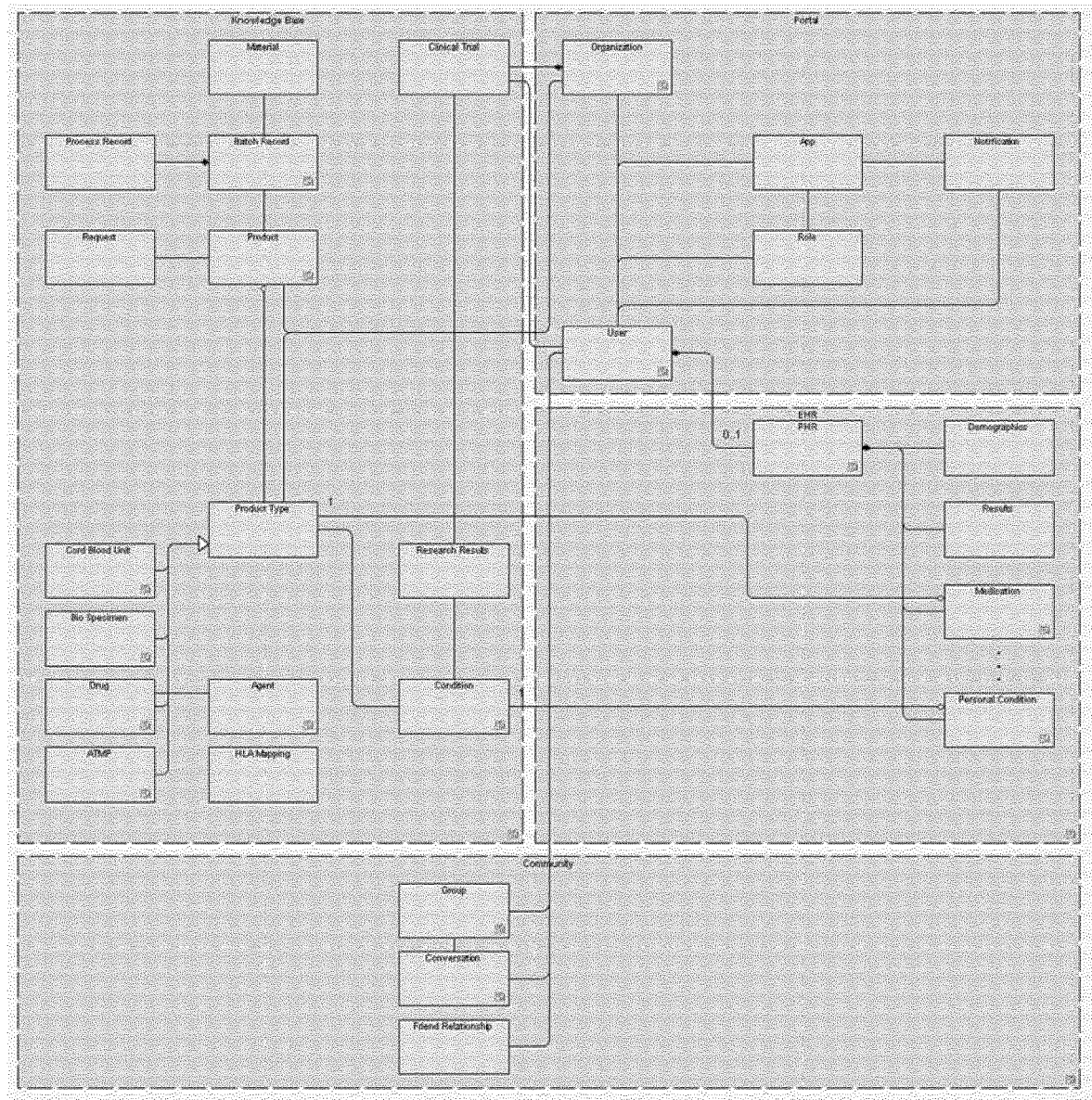

FIG. 10 depicts an entity-relationship diagram modeling selected entities of the Cytolon data model.

The platform data model follows the Fast Healthcare Interoperability Resources (FHIR) standard as defined by the Health Level 7 International (HL7) consortium [14]. It depicts the entities involved for management access rights: user, roles, and organizations. Furthermore, it depicts notifications, which are fundamental aspect of the messaging system of the invention to provide app-specific notifications to the user.

In addition, it depicts the Personal Health Record (PHR) of the user as primary storage of all user-specific healthcare data.

C. Software Components and Architecture Layers

Figure 11:
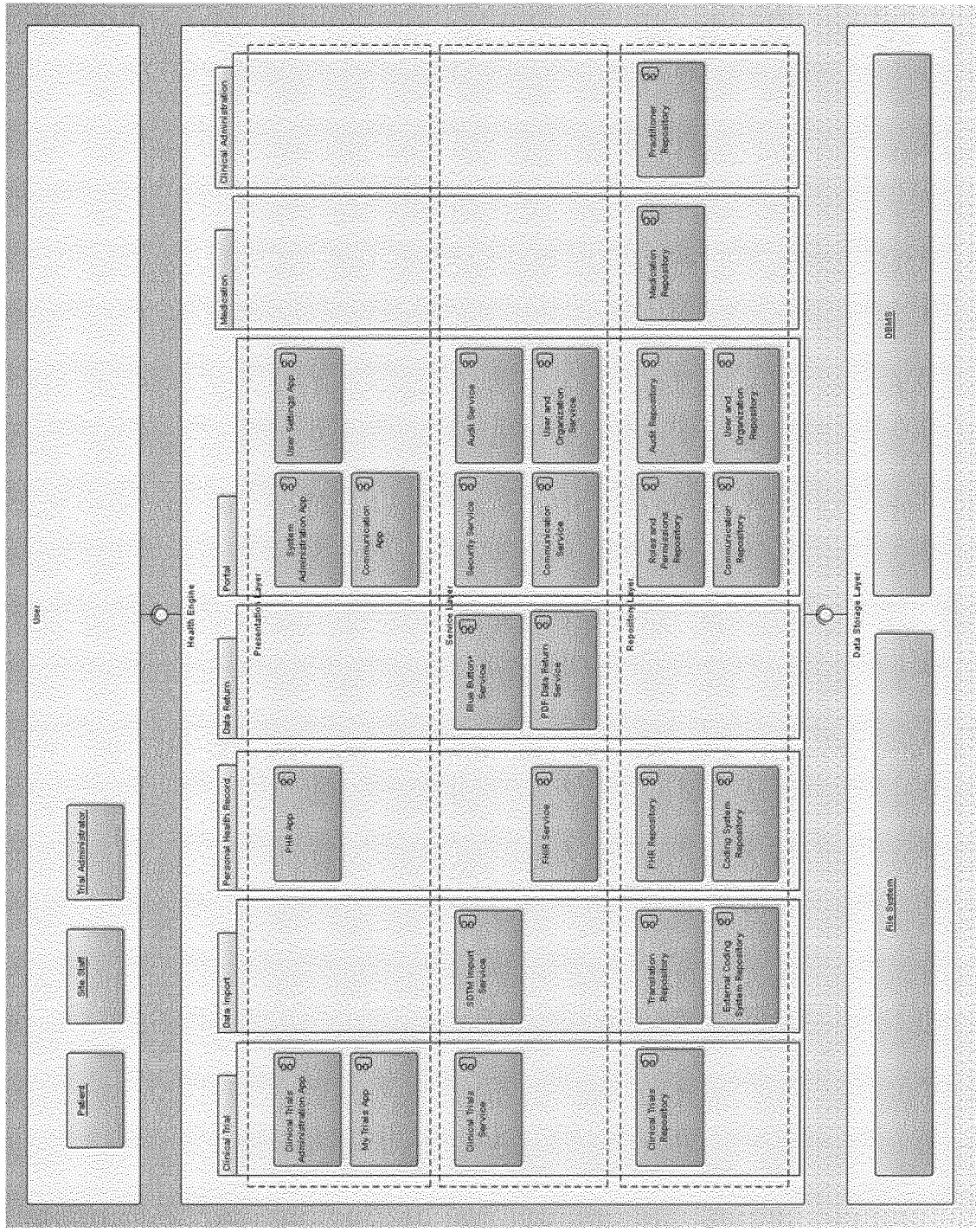
Figure 12:
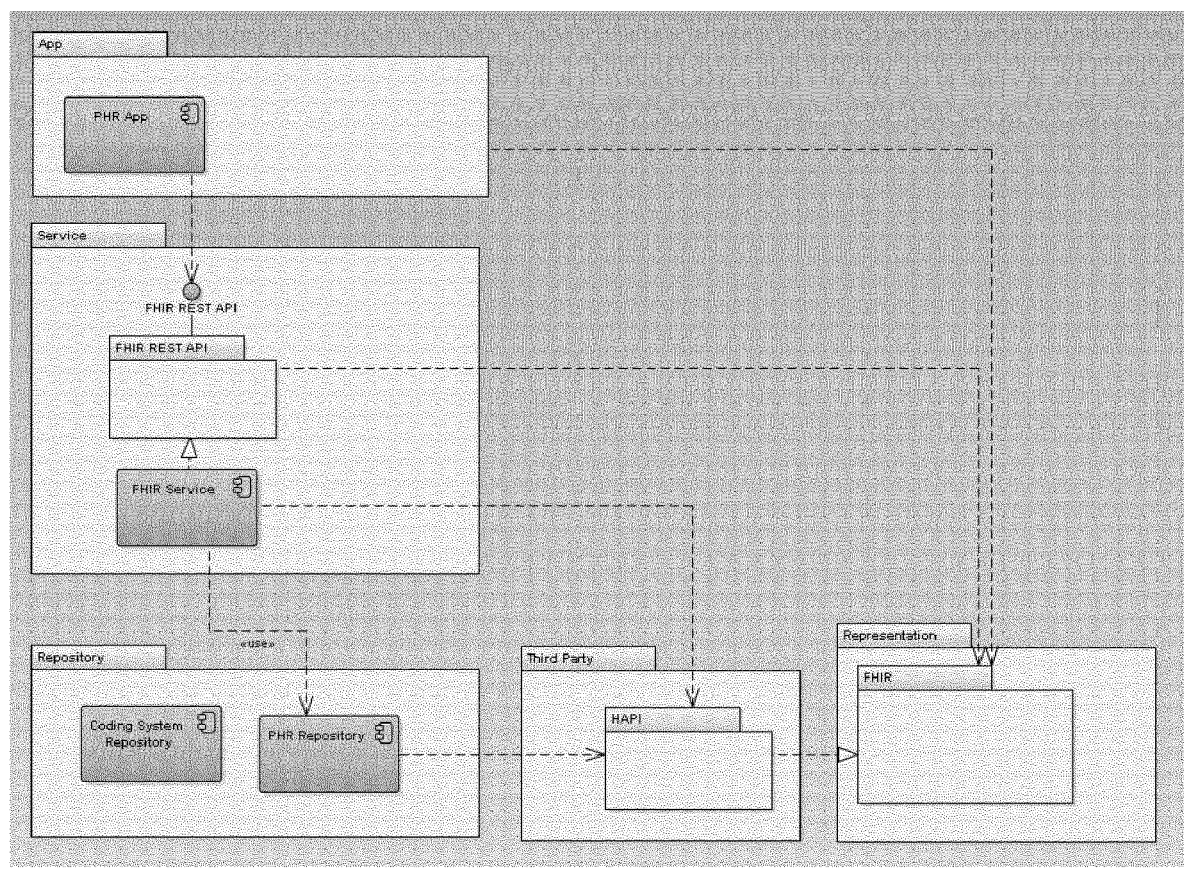

FIG. 11 depicts the interaction of selected components of the layers repository, service, and presentation of a preferred platform modeled as Unified Modeling Language (UML) component diagram [15]. FIG. 12 depicts the PHR as an example in a more fine-grained way across the defined layers of the system architecture.

VII. Platform Functions

In the following, we outline selected core apps or core modules of the platform. These modules are provided as an integral component of the system to have a common set of functionality available. These modules can be incorporated by any empowerment app to reuse core apps, such as searching and notes.

A. Personal Health Record

It is preferred that the PHR module comprises a central database for individual healthcare data, wherein data entries comprise a timestamp and a set of attributes and values.

The PHR is the central file for all individual healthcare data. Each entry consists of a timestamp and a set of attributes and values. The superset of all data forms a longitudinal database of personal healthcare data linking observations documented at certain points in time. The content of the PHR varies in format, size, and structure, i.e. structured and unstructured data. For example, unstructured data are medical documentation, discharge letters, images, raw genome data, videos, amongst others, whilst examples for structured data are results of allergies test, medication lists and history, doctor appointments, immunizations, care plans, letters of referral, diagnosis codes, lab results, e.g. blood tests, lists of genetic variants, vital data, amongst others.

As of today, individual artifacts of the personal healthcare data of a single patient are obtained and stored in individual software system, e.g. Physician Information Systems (PIS), Hospital Information Systems (HIS), or lab systems. Due to the variety of software systems and data formats, it is still a challenge to obtain a holistic view across all heterogeneous and distributed data sources especially for the patient, who is the owner of her/his own healthcare data. The invention's PHR enables the storing of all individual data in a centralized and secured databank, the single source of healthcare-related data for the patient. The PHR supports the transformation of individual data format into a homogenous data format of the platform of the invention. As a result, it contributes by the combination of data sources, the harmonization of data format, the export of data into a standardized data format, and the sharing with other systems and parties enabling secondary use of existing data, e.g. for doctors and research.

The PHR app provides basis functions, such as create, read, update, delete of personal healthcare data. In addition, it also links into the system-wide authorization module. Thus, the user is able to grant access to a subset of data to other user or user groups on the platform, e.g. family members, physicians, advocacy groups, pharma sponsors or researchers, while having full control over her/his data at any time, i.e. she/he can revoke the granted access at any time.

Tab. II provides a mapping of selected user stories to mockup figures.

TABLE II

| App | Role | User Story | FIG. |
|---|---|---|---|
| PHR | As a user | I want to see visualizations of my lab values so that I see their change over time. | 13 |
| PHR | As a user | I want to see each lab value in detail so that I know the exact value. | 14 |
| PHR | As a user | I want to download my PHR data in an interchange format so I have a machine-readable copy of it. | 15 |
| Sharing | As a user | I want to get an overview of all patients sharing their personal health record with me so I know which data I can access. | 20 |
| Sharing | As a user | I want to access the personal health record of a patient sharing her/his record with me. | 20 |
| Sharing | As a user | I want to search for a user so that I can share my personal health record with him. | 21 |
| Sharing | As a user | I want to get an overview over all users I share my personal health record with. | 21 |
| Sharing | As a user | I want to cancel my sharing with a user so that he cannot access my personal health record anymore. | 21 |
| Sharing | As a user | I want to receive a message when a patient shared his personal health record with me. | 21 |
| Sharing | As a user | I want to see visualizations of lab values of personal health records shared with me. | 13 |
| Sharing | As a user | I want to send messages to patients who share their personal health record with me. | 13 |
| Donation | As a user | I want to donate my personal health record data anonymously. | 22 |
| Donation | As a user | I want to change donation settings so that I do not receive messages based on the donation of my record | 22 |

B. Messaging

The messaging systems of the invention allows the creation, receiving, and exchange of messages with the user or user groups as an integrated feature for all apps or modules on the platform. It handles all messages from apps or modules and users, their routing, and the delivery to recipients. It also provides notification features, e.g. to send out mails short messages, or alert on the web page.

C. Regular Personalized Digital Newsletter

For each user of the platform, a personal weekly newsletter is provided with information carefully selected. The regular newsletters contains details about the trial the user participants in, e.g. number of total participants, weeks running, or potential trials she or he might be eligible for. In addition to program specific details, the newsletter also contains personal information, e.g. next steps in the trial or remaining time until the trial participation finishes. Thus, patients are enabled to keep track of their next steps and can ensure that corresponding actions are taken, which increases transparency.

D. Search

The Search used in the invention implements enables full-text search on personal data of the user across all apps of the invention, e.g. documents in the PHR, the Inbox, and community.

The search apps allows ranking, sorting, and filtering of search result as well as heuristics to identify most relevant results, e.g. fuzzy search, history search.

E. Blogging and Discussion Forums

The Blogging and Forums functionality enables user on the platform to create articles and publish them, e.g. for a certain audience or user group. Published articles are shared on the platform and initiate a communication thread. As a result, other users are able to publish answers, comments, or statements referencing on the initial article to create an ongoing discussion thread. By integrating the Blogging and Forums functionality into apps, it allows the generation of user-driven content. Aggregating the user-driven content results in a knowledge base, which can be extended by reviewed contributions by doctors, medical experts, professionals, etc.

F. Calendar

Users of the platform have a complete overview of their past and upcoming appointments using the Calendar functionality. Thus, they are able to manage their appointments and/or monitoring even outside of site's opening hours by sending updates to site staff, which will contact them for rescheduling. The calendar app is used for management of user specific healthcare-related appointments as in integrated components of the platform. For example, this functionality can be used to log upcoming visit appointments or updated appointments directly without involving the site staff. In combination with other services, automatic reminders for upcoming appointment can be set to send out automatic notifications for users.

G. Notes

The Notes app enables users to note down individual notes and store them within their personal profile. Taken notes are considered as normal data objects, which can be shared with other parties similarly to the user's PHR. The notes functionality on the platform can be integrated within other applications, e.g. to annotate lab results or to document self-reported outcomes in free-text.

H. Application Store and Ecosystem

The host's App Store provides the user of the platform a holistic view on available apps and tools. It summarizes all available apps of the invention as well as certified third-party apps. In the app store, detailed information is shown for each app, e.g. name of the app, description, version, and app icon, including possible modal actions the user can initiate, e.g. subscription or unsubscription. Access to apps depends on user-specific criteria, e.g. user roles, participation in a certain trial or program, legal regulations of the user's country. The user can initiate the subscription to application directly. The use of applications might involve user payments, e.g. in advance, regularly part payments during its use, or after the end. Applications are aggregated in categories to make it easier to find relevant apps.

The following apps—amongst others—are incorporated by the app store:

The Search app enables the search and filtering of apps
The Rating app enables users to rate individual apps I. Location-Based Services It is preferred that users can filter and order any kind of data results accordingly to a specified location and/or their current location with the location-based services module The Location Services app of the platform enables user to rank any kind of data results accordingly to a specified location or their current location. For example, the location services improve the relevance of search results, e.g. when finding an investigator, hospital site, pharmacy, or patient advocacy group near the user's current or home location.

J. Rating

The Rating app allows documenting quick reviews of selected artifacts by users on the platform. For example, user can rate physicians, investigators, CROs, and services on a user-defined scale. Rating results are only accessible in an aggregated form, i.e. no conclusion on concrete ratings of individuals is possible after their participation.

K. Payment Services

The Payment app allows the initiating and processing of payments on the platform, e.g. for subscription to apps or services. The service allows the integration of various payment services, e.g. credit card, bank transfers, and online payment services. It also provides the required services for reimbursement of users, e.g. to distribute financial incentives.

L. Data Exploration and Analytics

It is preferred that the system comprises a data exploration and analytics module which allows real-time exploration and analysis of data stored on the platform and/or flexible selection and filtering of specific subsets of data to meet user requirements and the combination across a variety of available data sources.

The Data Exploration and Analytics app of the platform is designed for all actors. It allows the real-time exploration and analysis of big medical data stored on the platform, e.g. in graphical, tabular, or raw format. Furthermore, allows flexible selection and filtering of specific subsets of data to meet user requirements and the combination across available data sources. The purpose of the app is to explore big data sets with the aim to detect patterns, verify research hypotheses, and to identify correlation between attributes. Thus, the app turns raw data into insights and support better understanding and interpretation of acquired data as a consequence.

VIII. Patient Empowerment Apps

In the following, we outline empowerment apps of the platform. Empowerment apps build on platform services and core modules to create a value-added app for users. Empowerment apps can either be provided by the host or certified third parties to extend the functionality of the platform.

It is further preferred that the empowerment apps are selected from the group comprising opt-in app, data return app, data sharing app, data donation app, personal message inbox app, tasks app, medication history app, pharmaceuticals and medication alerts app, investigators and doctors app, community and social network app, disease and treatment knowledge base app and/or personal performance dashboard app.

Tab. III defines a mapping of apps to communication methods. (A, B=uni-directional, C, D=bi-direction, A,C=triggered by user, B, D=triggered by investigator or site).

TABLE III

| App | A | B | C | D |
|---|---|---|---|---|
| Opt-In App | | | | ✓ |
| Data Return App for Personal Clinical Trial Data | | ✓ | | |
| Data Sharing App | ✓ | | | |
| Data Donation App | ✓ | | | |
| Personal Message Inbox App | ✓ | ✓ | ✓ | ✓ |
| Tasks App | ✓ | ✓ | ✓ | ✓ |
| Medication History App | ✓ | | | |
| Pharmaceuticals and Medication Alerts App | ✓ | ✓ | | |
| Investigators and Doctors App | ✓ | | | |
| Community and Social Network Apps | ✓ | ✓ | ✓ | ✓ |
| Disease and Treatment Knowledge Base App | ✓ | ✓ | | |
| Personal Performance Dashboard | ✓ | | | |

A. Opt-In App

In a preferred embodiment the invention relates to the system further comprising an opt-in app, wherein an opt-in process involves patients, investigators and clinical research associates, wherein patients provide their consent preferred to the terms of use or the participation in a clinical trial, the investigators explaining the service and supporting the patient, and clinical research associates act as representative of the sponsor.

The foundation of reducing barrier for users to participate, e.g. in specific program, routine, or screening, is the provision of the personal consent. The platform bridges the gap by providing management of electronic consent for users at any time.

Figure 16:
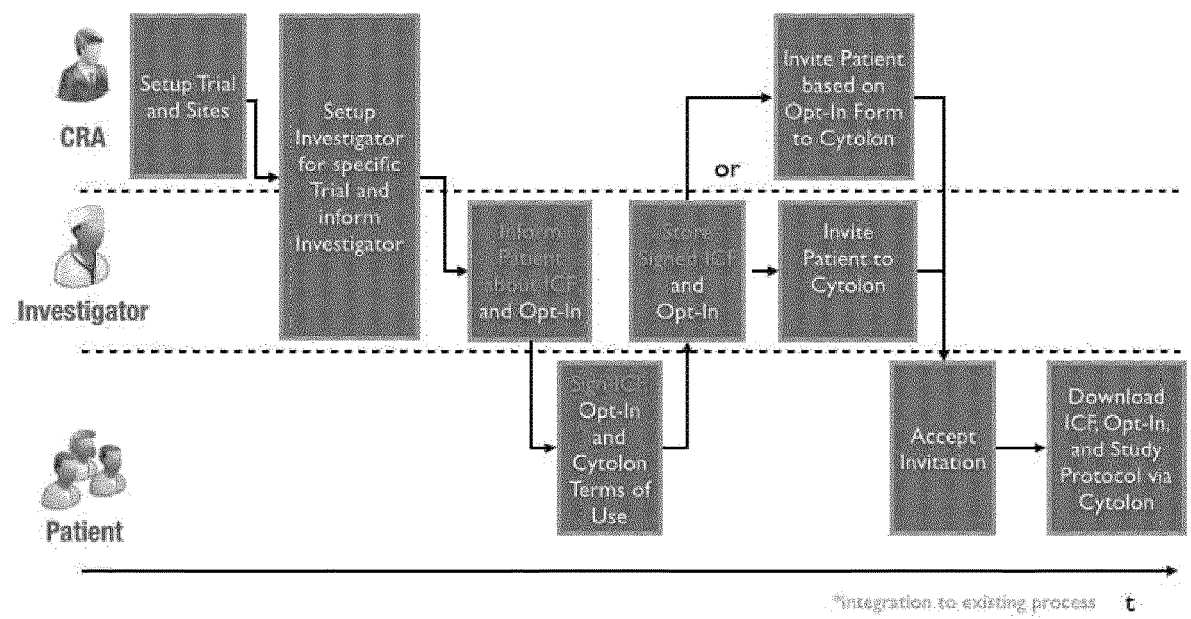

The "Opt-in" process depicted in FIG. 16 involves the following users of the platform:

Patients to accept the terms of use and to sign-up for the "Opt-in" service,

Investigators to introduce the service and support the patient, and

Clinical Research Associates (CRAs) acting as representative of the sponsor.

The CRA sets up the trial in the system and creates associated sites. Afterwards, she/he can set up and invite involved investigators for every created site. The investigator will receive an invitation email and can register to the system. Typically, the CRA will introduce the investigator in a "site investigator meeting" to the system.

Once the investigator has activated his account and was introduced to the process by the CRA he will inform patients on the data return option in the clinical trial. When signing the ICF for the trial the patient is offered an additional "Opt-in" form that he needs to sign to get his trial data back via the Health Engine Service. The Opt-in form will be signed in written form and the investigator will store the document. In addition to the consent that platform host is allowed to retrieve her/his trial data the patient will allow the host to contact him on behalf of the sponsor.

The main information that is to be retrieved via the Opt-in form is first name, last name, and email address. The investigator will then either invite the patient to the platform himself or, more likely, transmit the Opt-in information to the CRA who will then invite the patient. The patient can be invited to the trial on the Health Engine by providing his name, email address and the subject number within the trial. Afterwards, the patient will receive an invitation, which will lead him to the Health Engine registration where he needs to accept the terms of use before being able to enter the system.

Figure 17:
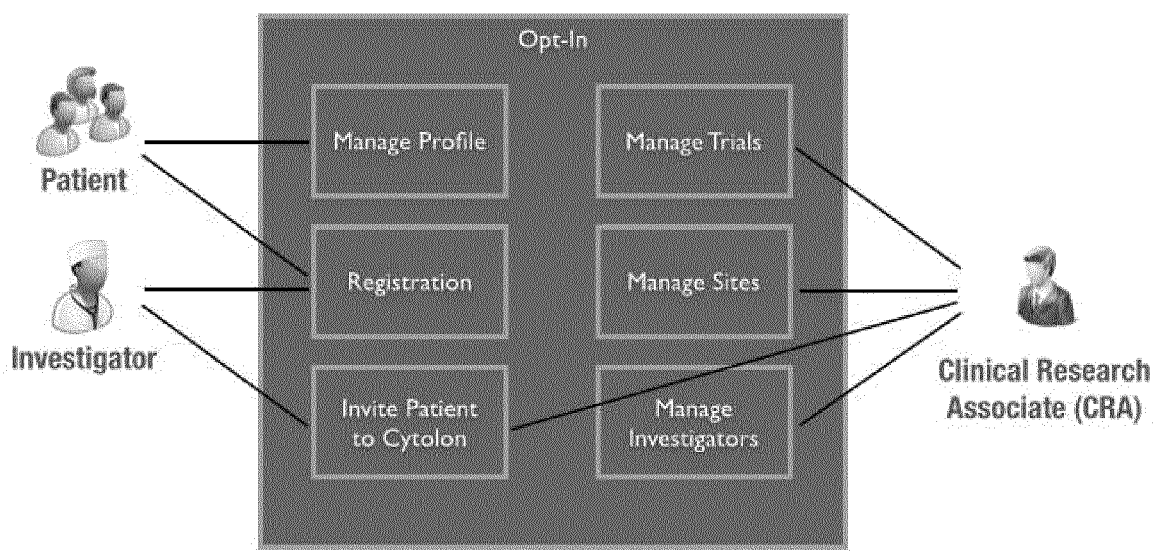

FIG. 17 summarized the following use cases defined for the Opt-in process:
- The CRA shall be able to set up clinical trials, sites and investigators in the system,
- The investigator and the CRA shall be able to invite patients that opted in to clinical trials,
- Patients and investigators shall be able to register to the application upon invitation, and
- Patients shall be able to manage their profile and "Opt-in settings" like who is allowed to contact them.

The Opt-in app allows acquiring the personal consent of the user for selected activities, e.g. participation in a program and use of samples or data. As a result, the consent app allows direct interaction between user and sponsor even after the end of the participation in a clinical trial, which streamlines the acquisition of the legal consent and re-consenting for secondary use of samples or data. The opt-in app also allows the user to review the latest consent at any time. For changing a consent, the user either can use perform the necessary changes directly on the platform, i.e. she or he can update any given consent at any point in time, or if the consent is not directly editable due to program restrictions, the user will be forwarded to contact site staff to perform the necessary actions. Any change in consent will be logged in the platform to form a complete history of consents and their status at any point in time, which increases transparency for the user.

B. Data Return App for Personal Clinical Trial Data

It is especially preferred that the system comprises a data return app, wherein the data return process comprises the sponsor being able to provide CRF data, the CSR, a lay summary, a patient-specific summary, patient-specific trial data, and to inform the patient and the investigator on its availability via the system being able to view and download the returned data via the system.

As we consider patients as the owner of all patient specific data, we believe that the access to these personal data is the quid pro quo for users of the platform. As a result, the platform allows access to personal data, e.g. obtained during screening, lab test or trial participation, in a standardized electronic format, e.g. to exchange data with other IT systems, and in a human-readable format, e.g. to exchange with friends and family members.

Figure 19:
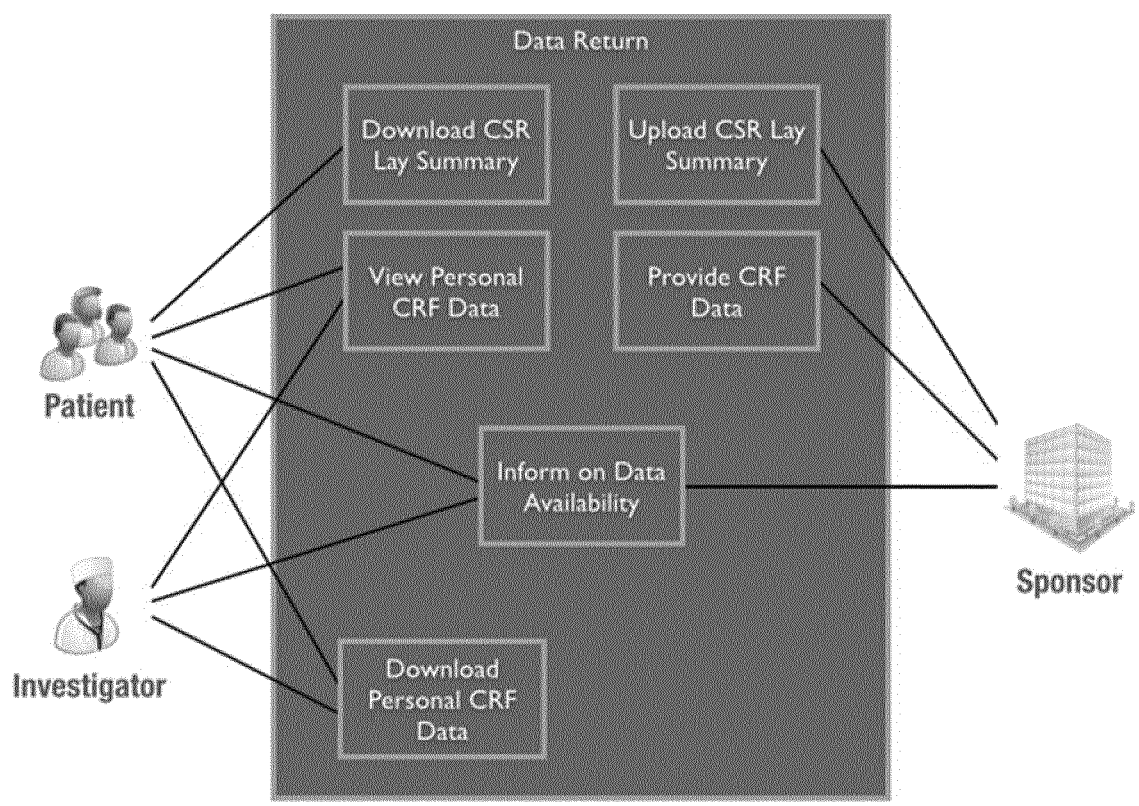

FIG. 19 summarized the following use cases of the Data Return process:
- The Sponsor shall be able to provide CRF data and CSR lay summaries and inform on data availability via the system, and
- Patient and investigator shall be informed on data availability and be able to view and download the returned data via the system.

Figure 18:
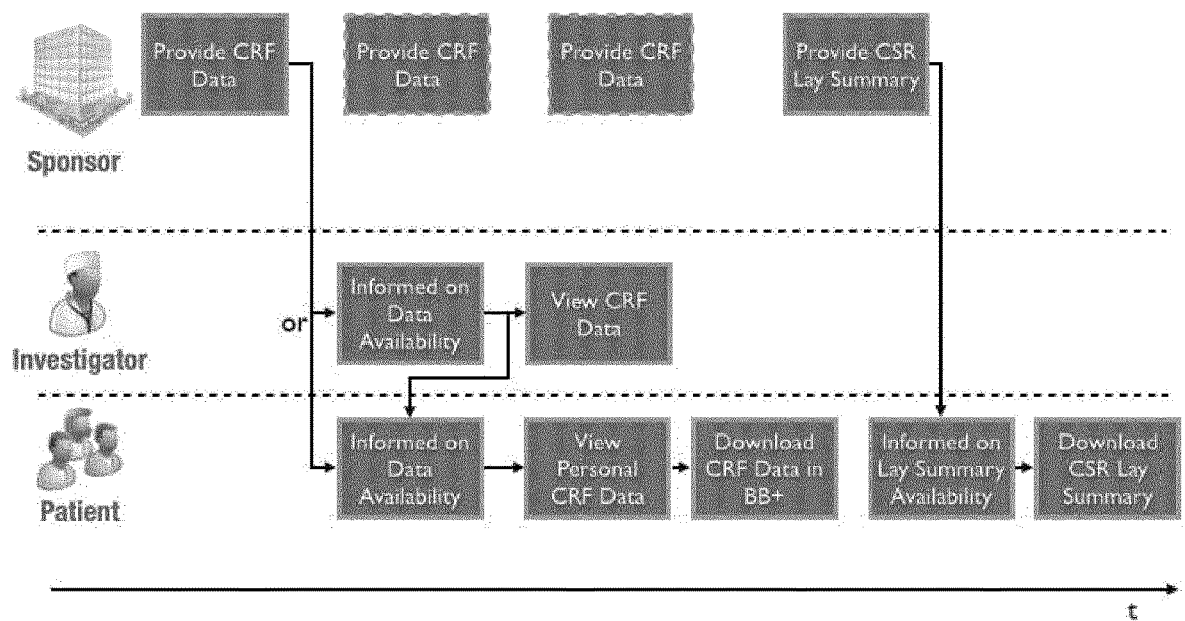

FIG. 18 shows the data return process involving the user types "Sponsor", "Investigator" and "Patient". For the sponsor the most likely roles to perform the data provisioning from the source system to the Health Engine are "Data Manager" or "System Administrator".

The sponsor will provide the CRF data of the trial participants to the Health Engine. The required interfaces and data conversions need to be implemented beforehand. Investigators and patients related to the trial are informed on data availability as data becomes available. A patient and his investigator can then access the view the provided data within the system. This allows investigators to refer to the returned data in case of patient inquiries.

Additionally, the patient is able to download the returned trial data in a standardized data format, e.g. the Blue Button+ format, a clinical study report, and a lay summary upon availability [16]. The data return process may occur several times for a trial in case data is also provided at intermediate points during the trial.

C. Data Sharing App

It is also preferred that the system comprises a data sharing app, whereby users can share their personal healthcare data with selected users or user groups with the data sharing app comprising
creating a set of data items,
bundling the data items to a data set,
creation of a unique identifier, which will be accessible by the users or user groups with the appropriate privileges only while access privileges granted.

The data sharing empowers users to share their personal healthcare data with selected users or user groups individually, e.g. family members, friends, and patient groups. The user keeps full control about the shared data sets and can revoke any granted rights at any time. The user initiates the data sharing by creating a set of data items, bundles it to a data set, which is managed as resource in terms of the rights management. Sharing data does not necessary involve export or copying, but the creation of a unique identifier, e.g. URL, which will be accessible by the users or user groups with the appropriate privileges. The owner of the data set may update the access rights at any time so she or he always has full control about who accesses the shared data. In addition, the user can be notified about any access to the data in the app to keep a complete history of exposed data sets.

D. Data Donation App

With data donation, users of the platform are able to donate selected personal healthcare data to selected parties, e.g. researchers. As a result, they can contribute to drive healthcare research forward by enabling clinical researchers access to real-world data for specific indications. Data donation works similar to data sharing whilst you do not know the concrete person in advance, who might access the data. As a result, donating data does not result in a 1:1 knowledge of sharing party and using party keeping booth anonymous.

E. Personal Message Inbox

Figure 23:
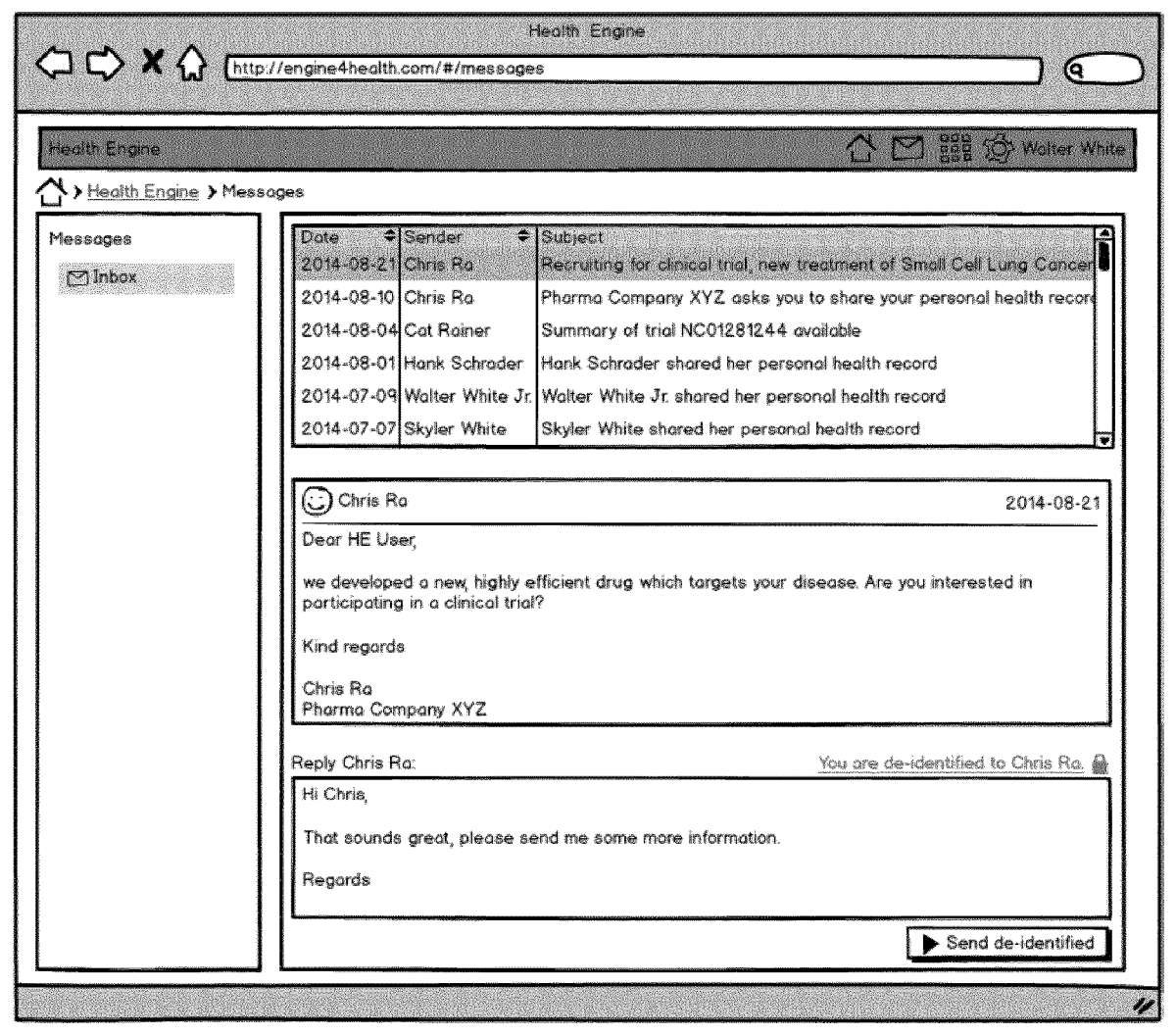

The Personal Inbox app as depicted in FIG. 23 is the central aspect of the platform's messaging system. Any kind of information addressed to the user will be delivered and stored here. Information stored in the inbox are, amongst others, system status messages, personalized messages from sponsor, investigators, or researchers reaching out to the patient, patient engagement information, personalized surveys, and messages from social media channels.

The inbox is also the key component for keeping the identity of the user private and ensuring no unintended disclosure during any kind of communication, e.g. when being in contact with the sponsor or researcher groups.

As a result, all personal messages for the patient will be delivered into the inbox by the messaging system, which prevents exposure of personal information by masking the recipient and sender's address, e.g. replacing it by the sponsor's subject and clinical trial identifiers. Once new messages are available in the inbox the user will be notified via selected communication channels to log into the inbox to access the new messages. The communication channels are configurable in personal user profile, e.g. amongst others, email to a defined private address or text messages to a cell phone number.

F. Tasks App

A personal task list helps to organize and stratify the organization of the user's daily life. As a result, the platform provides the management of personal tasks as an integral functionality. Tasks can be created either by users or applications. Tasks can have a due date, which will trigger a notification on or before the due date. The Tasks app enables the patient to keep track about personal upcoming tasks, e.g. tasks in the course of the participation in a clinical trial. FIG. 24 depicts a checklist for a certain patient. It contains a list of individual upcoming tasks for the patient. Entries in the task list are either defined by the user or by the system, e.g. as part of the participation in a certain program.

G. Medication History App

In the Medication History app is linked to the user's PHR and enables them to log their currently taken drugs to form a complete history of mediation. In addition, prescribed medications in the course of a clinical trial or program participation will be added here using the data return app. Once drugs are added to the app, the user can subscribe to additional services, e.g. medication alerts.

H. Pharmaceuticals and Medication Alerts App

The Pharmaceuticals and Medication Alerts app is used to notify subscribed users about latest alerts about pharmaceutical released by official sites, e.g. the German Federal Institute for Drugs and Medical Devices (BfArM) or the U.S. Food and Drug Administration FDA [17], [18]. Amongst others, pharmaceutical recalls, new leaflet information, additional side effects or change in drug interactions, are events, which can trigger an alert that will be sent forwarded via the personal Inbox to the user. For the proper function of the alert app, it accesses selected patient-specific data, e.g. the medication history and the PHR. Furthermore, the app allows users to log personal notes about their experiences with a certain drug they take, e.g. to share with other users or user groups via the notes.

I. Investigators and Doctors

The Investigators and Doctors app assists users of the platform in finding investigators, e.g. participating in particular clinical trials near their family homes. In addition, the app provides for investigators the feature to setup a personal portfolio containing information about their special fields of expertise. Furthermore, investigators can add trial-specific information, such as number of clinical trials, number of completed studies, or rating.

The app allows users to share notes, personal feedback with other users or user groups as well as rate their last visit experience to provide customer feedback for investigators via the messaging system while keeping their identify private. Furthermore, users of the platform can manage their existing or create new appointments with selected investigators and doctors via the calendar app.

J. Community and Social Network Apps

The platform provides a Community and Social Network app, which provides functionalities, amongst other, to create and manage relationships, e.g. friends, family, doctors, send and receive personal and group notifications, as well as the exchange of any kind of social media data, e.g. videos, images, photos, voice, music, contacts, chat messages, etc. Each user will be able to create a personal profile consisting of individual information. Users may use provided profile templates or extend it also with any personal data. All provided data is considered as resource in terms of the access control, i.e. the user can control what resource is exposed to specific user group, such as public, friends, and family. Each platform user can manage members of personal user group individually.

The app provides functions to create, read, update, delete relationships and exchanged data.

K. Disease and Treatment Knowledge Base

The Disease and Treatment Knowledge Base (KB) app summarized various specific data sources around individual topics of interest, e.g. indications, diseases, treatments, in a standardized and harmonized way. It may contain various kinds of data, such as scientific publications, journals, wiki pages, links to web resources, images, news articles, books, PDFs, etc., including meta data for searching and filtering. The content of the KB can be curated or extended by users with specific access rights, e.g. medical experts or program members. The app provides functions to upload, create, update, and delete content interactively. The purpose of the KB is to provide relevant educational material for users with specific requests.

L. Personal Performance Dashboard

The Personal Performance Dashboard provides a graphical overview about selected personal key figures, e.g. days active, number of patients similar like you, available clinical trials, self-reported outcomes as time series, or upcoming events. Thus, it provides an easy understandable insight in big data and uses data analytics functions.

In another preferred embodiment the invention relates to a computer implemented method for use in the course of a clinical trial and/or precision medicine wherein metrics are acquired, which are documented as data points in longitudinal database accessible by users, and wherein core modules are provided selected from the group comprising personal health record module, messaging module, newsletter module, search module, blogging and discussion forums module, calendar module, notes module, application store and ecosystem module, location-based services module, rating module, payment services module, data exploration and analytics module, and wherein methods and/or automated services are provided, selected from the group comprising retention service, rewards and incentive service, patient education service, reminder service, medication adherence and compliance service, self-reported outcomes, surveys and questionnaires service, community and social network service, reimbursement service, campaign service and/or NB testing and wherein empowerment apps build on platform services and/or functions.

It is especially preferred that the computer implemented method makes use the system of the invention. Therefore, all preferred embodiments of the system are preferred embodiments of the computer-implemented method.

It is further preferred that the computer implemented method is not only used during the course of a clinical trial but also afterwards.

It was surprising and not expected that the special combination of modules, methods/services, apps and selected metrics results in a system and/or method for use for use in the course of a clinical trial and/or precision medicine which clearly demonstrates an improvement over the current state of the art.

The teachings of the present invention are characterized by the following features:
- departure from the beaten track
- a new perception of the problem
- satisfaction of a long-felt need or want
- the simplicity of the solution, which proves inventive action, especially since it replaces a more complex doctrine
- the achievement forwards the development
- young field of technology
- combined invention; a combination of a number of known elements, with a surprising effect Said advantages are shown especially in the preferential embodiments of the invention.

Example and Figures

Use Case

In the following, we outline a concrete use case for the Patient Empowerment Platform. In the remainder of this work, we consider the following persona. We share a concrete use case of Forrest G., who is concerned about his personal lung cancer treatment, and we outline how he uses selected tools and apps on our platform to increase his personal engagement.

Persona:

Forrest G., male, 62 years old, and smoker for a long period was just recently diagnosed with Non-Small Cell Lung Cancer (NSCLC). The patient worries about best available treatment for NSCLC Thus, he learned about targeted therapies and is very interested in participating in clinical trials optimized for his personal disease. Forrest wants to learn all about his personal performance in course of his treatment and wants to be aware about all treatment options available for him. His doctor informed him about the system of the invention providing him a leaflet. As a result, Forrest registered his personal account on the platform online. In the following, we outline a selected way to access and use the system as a patient. The given example shows only a limited functionality for this use case. The invention is not limited to this example.

Forrest G. uses the user-facing web app of the Patient Engagement Platform—amongst others—as follows:
- Forrest receives e-mail notification about new messages in his personal inbox on the platform
- He logs into his personal account on the platform to see available actions and key figures on his personal dashboard on the user-facing homepage,
- Forrest navigates to the Personal Message Inbox App. He reads his message that informs him about his eligibility for a clinical trial targeting NSCLC. Prior to additional screening his personal opt-in is required,
- He navigates to the Opt-in App to grant personal consent for further screening for the NSCLC trial,
- Forrest successfully passes screening at his doctor's site and gets enrolled in the clinical trial. He performs his regular doctor visits to receive a specific chemotherapy,
- After each visit, the sponsor of the clinical trials provides lab data. Thus, Forrest navigates to the Data Return App to access his personal lab data. He can access this and other health data stored in his personal health record on the platform

LIST OF FIGURES

Figure 2:
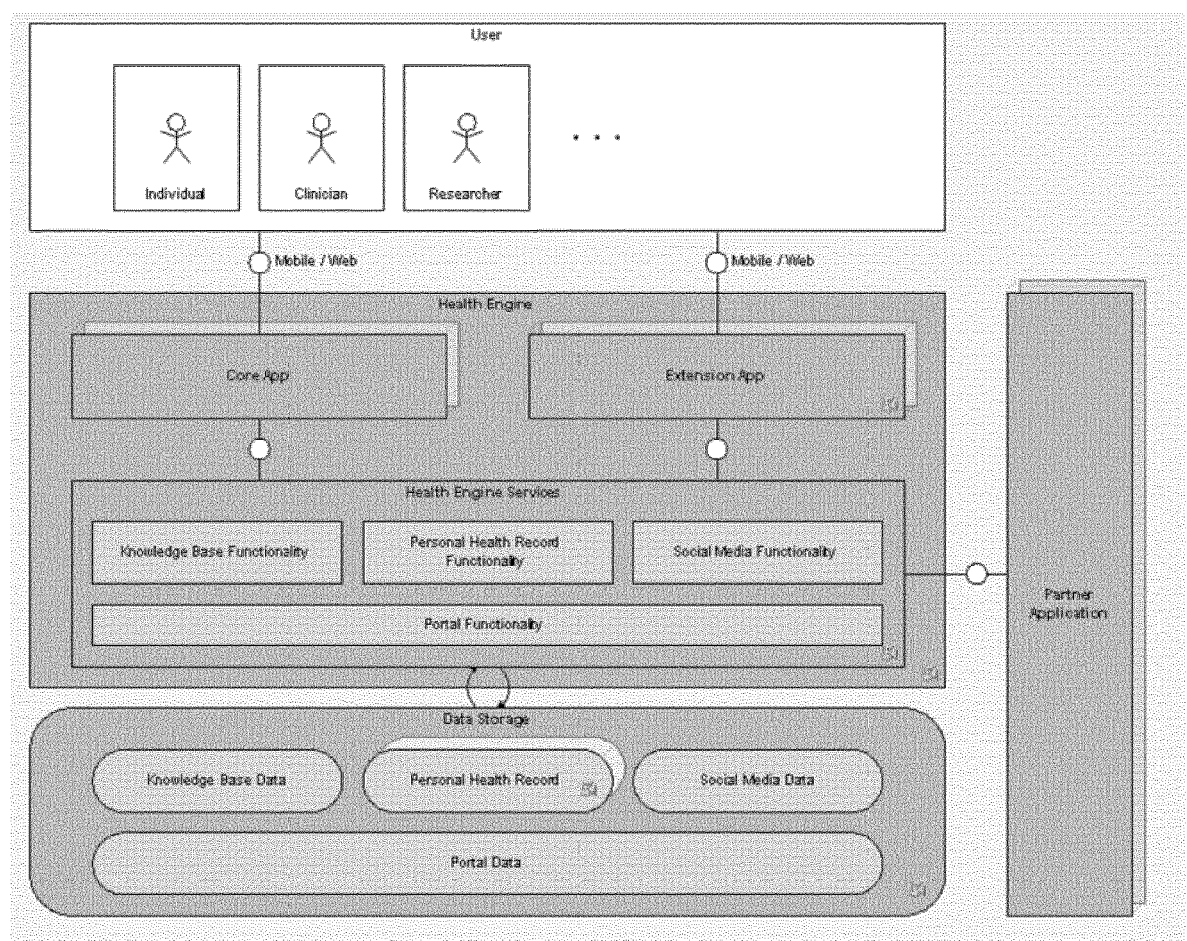

FIG. 1: The platform transforms patients into partners of research: constant bidirectional communication during, partnering and follow-up prior and after the clinical trial FIG. 2: Preferred software architecture model of the patient empowerment platform modeled as block diagram using Fundament Modeling Concepts (FMC) [4].

Figure 3:
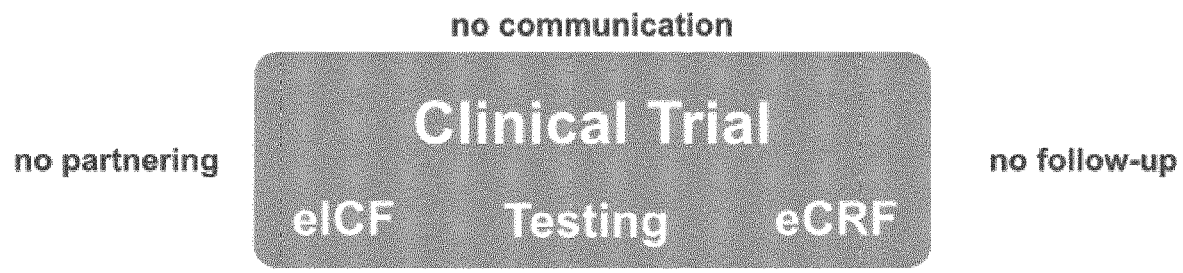
Figure 5:
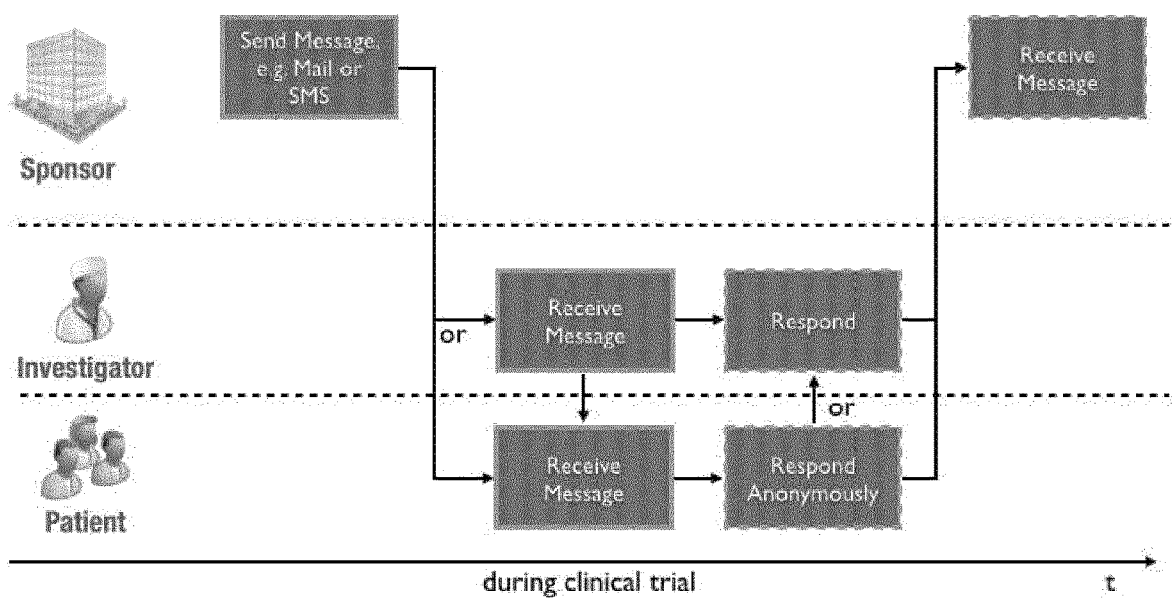

FIG. 3: The setup of clinical trials as of today: no communication during and no partnering and follow-up prior and after the clinical trial FIG. 4: Use case diagram of the patient retention process FIG. 5: Process model of the patient retention process FIG. 6: Process model of the patient follow-up process FIG. 7: Interaction of apps and services of a preferred platform of the invention FIG. 8: Entity relationship diagram for role-based access control implemented in a preferred software architecture FIG. 9: Entity relationship diagram for user roles across selected software components of a preferred platform FIG. 10: Excerpt of a preferred data model as entity relationship diagram FIG. 11: Software components of the platform modeled as UML component diagram FIG. 12: Layered software architecture model using the example of the PHR app depicting the app layer (user interface), the API layer (service interface), and the data repository (data persistence)

Figure 13:
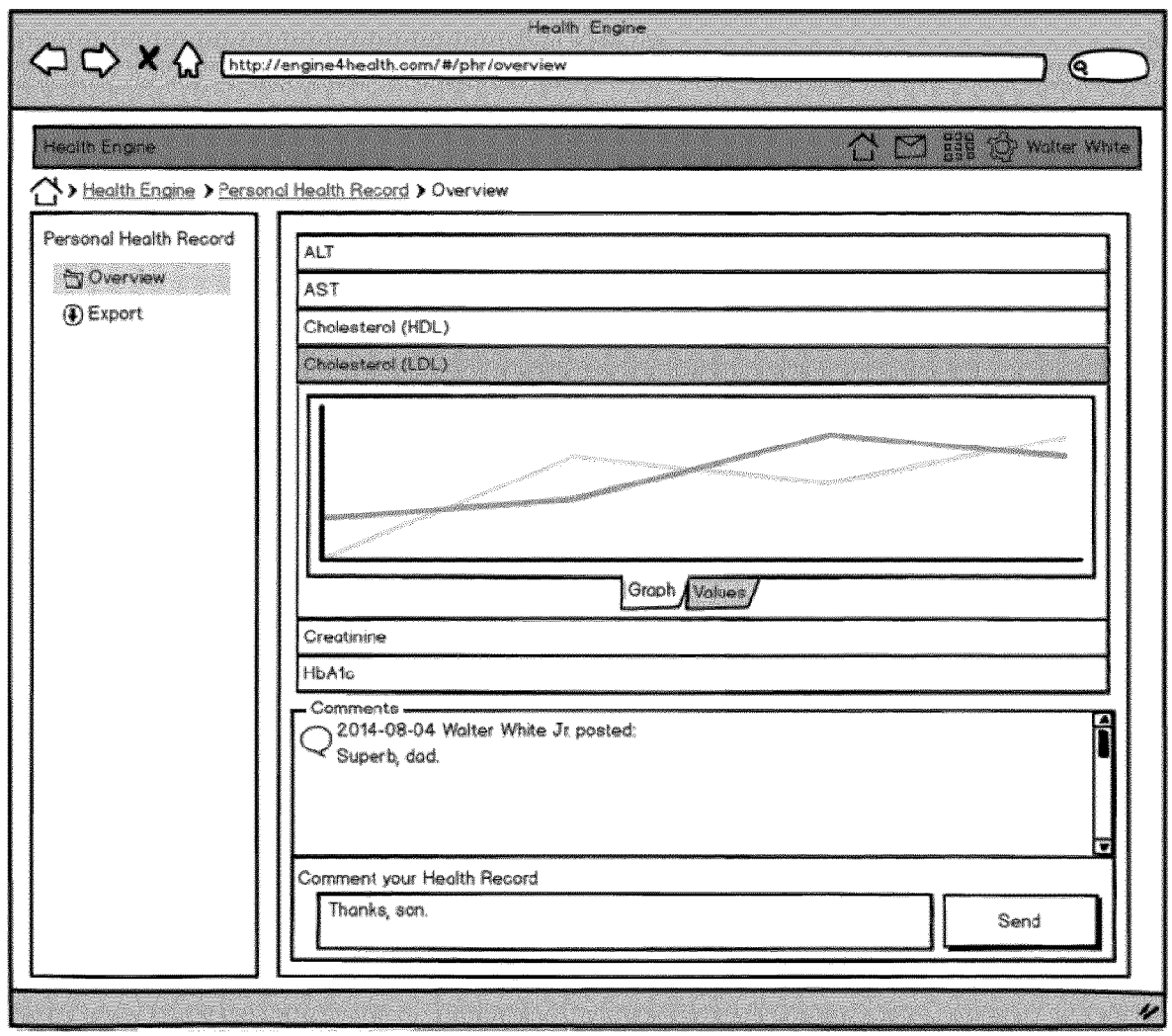
Figure 14:
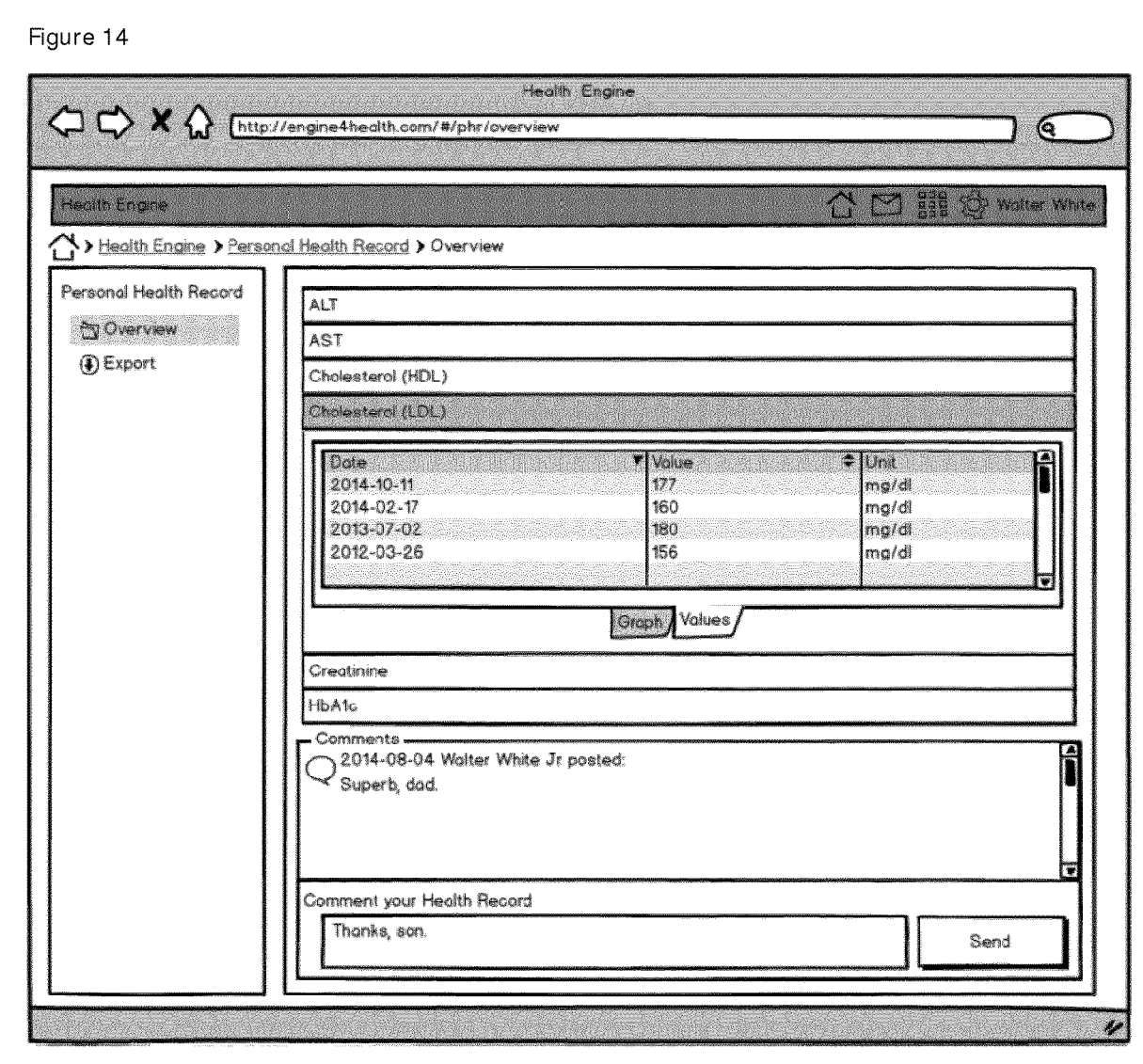
Figure 15:
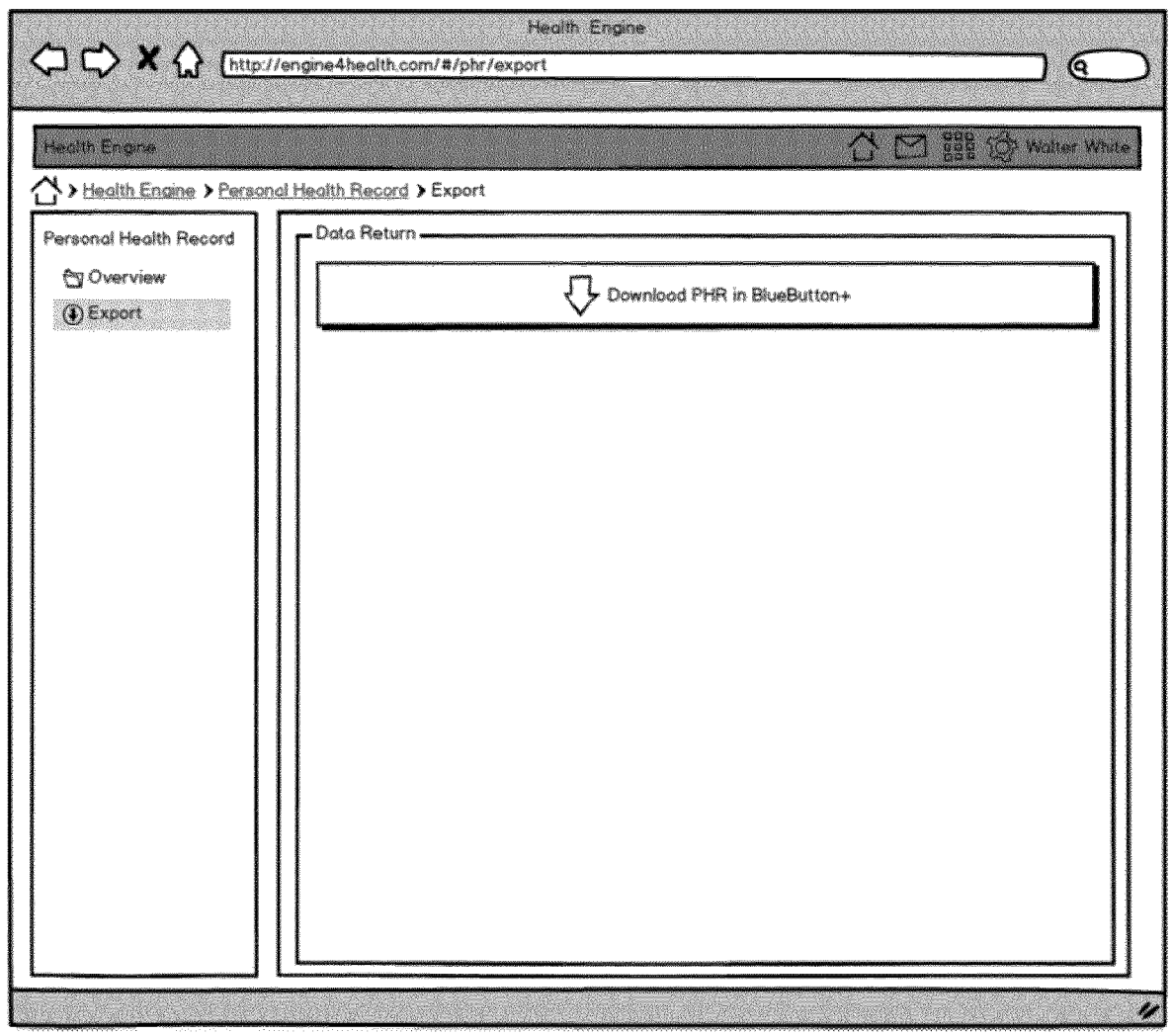

FIG. 13: Personal Health Record app depicting graphical representation of history of lab results FIG. 14: Personal Health Record app depicting lab results details FIG. 15: Personal Health Record app depicting the export function of personal data.

FIG. 16: Process model of the opt-in process

FIG. 17: Use case diagram of the opt-in process

FIG. 18 Process model of the data return process

FIG. 19: Use case diagram of the data return process

Figure 20:
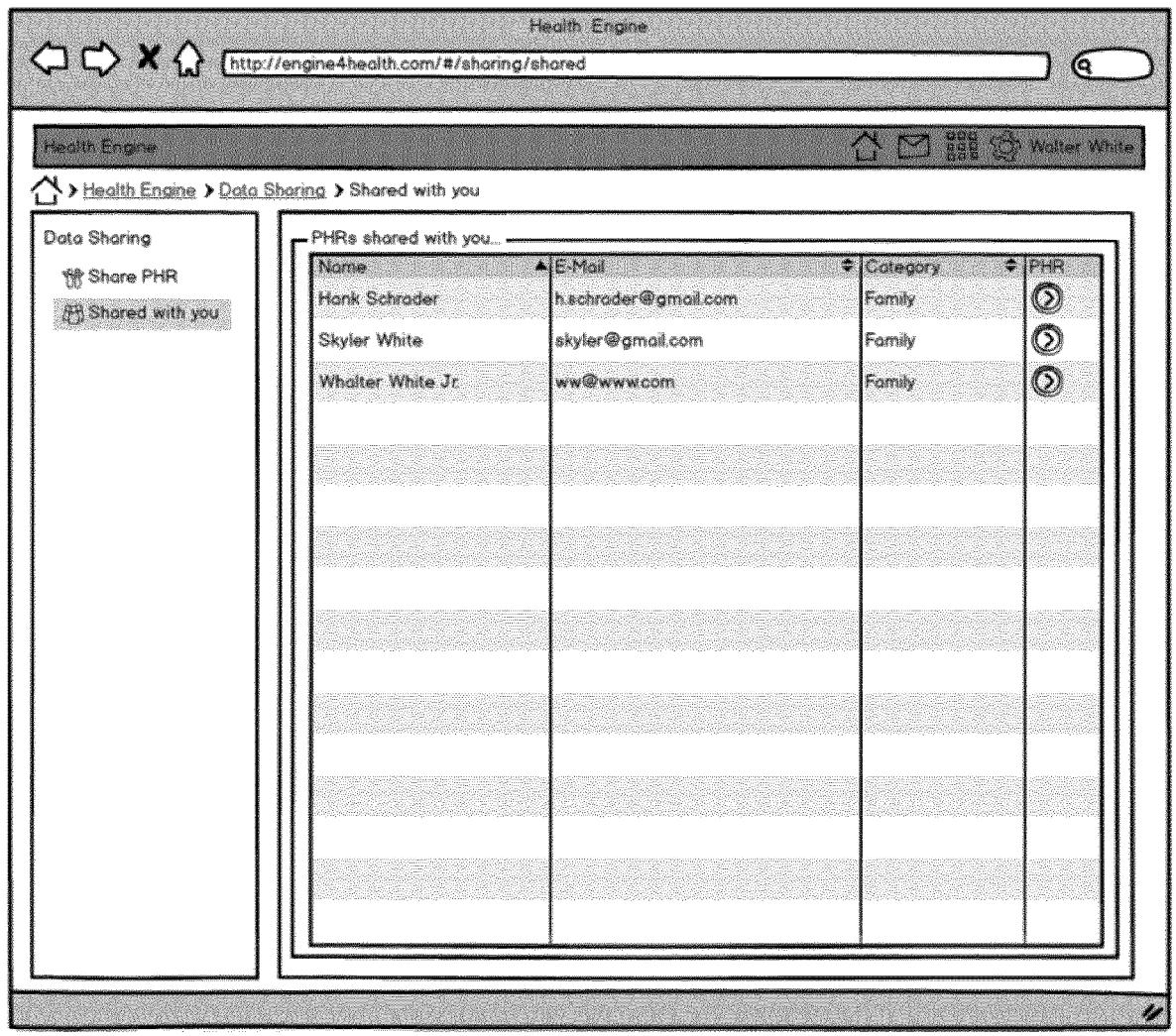

FIG. 20: Data Sharing app depicting the overview screen

Figure 21:
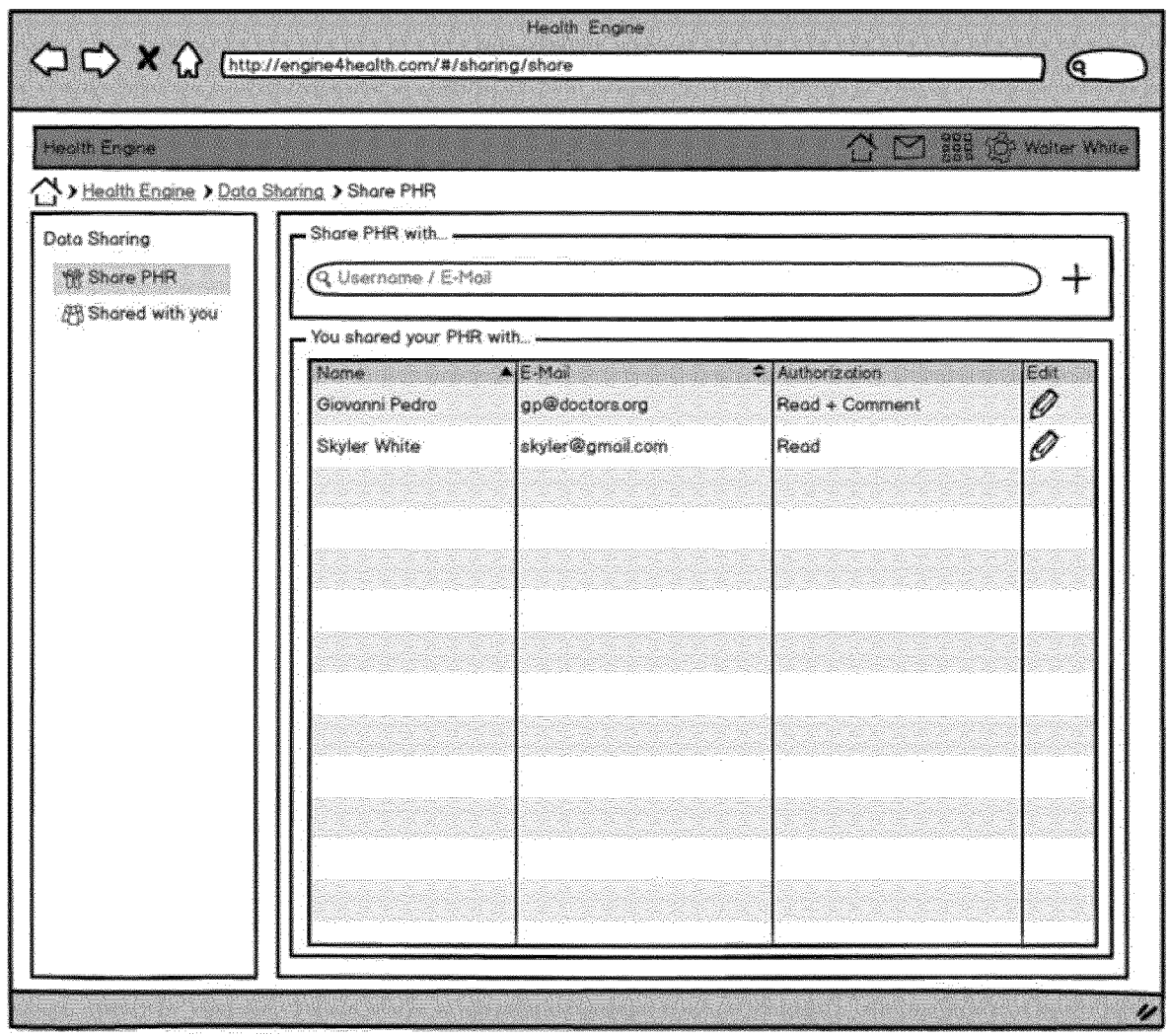

FIG. 21: Data Sharing app depicting the configuration screen

Figure 22:
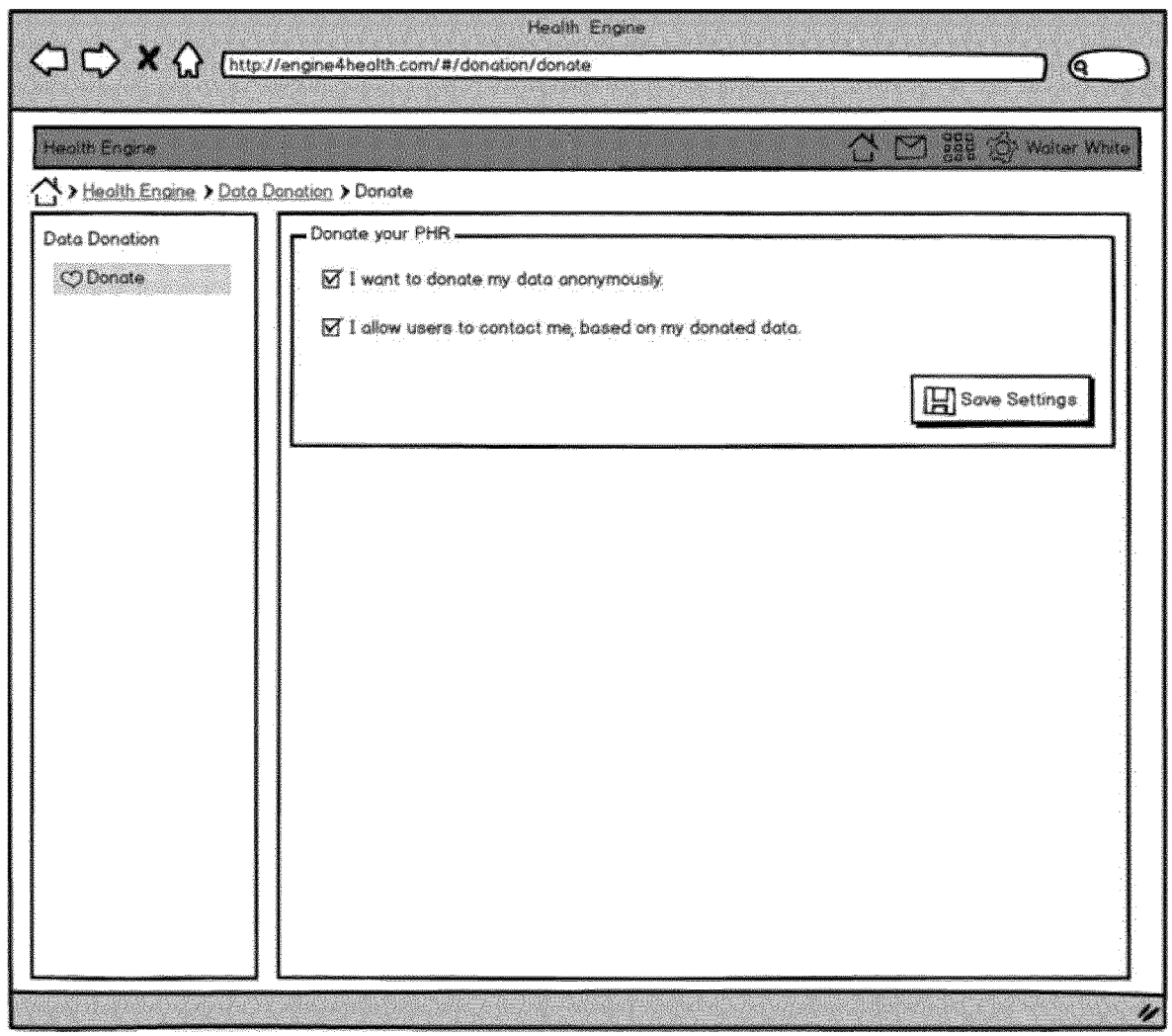

FIG. 22: Data Donation app depicting the configuration screen

FIG. 23: The message inbox contains all personal messages and enables the user to reply to them while remaining de-identified for pharma sponsors FIG. 24: Digital checklists are used to improve the participant's understanding about next

REFERENCES

[1] World Health Organization, "Handbook for Good Clinical Research Practice (GCP)," http://apps.who.int/prequal/info_general/documents/GCP/gcp1.pdf (last accessed: Mar. 25, 2015).

[2] W. R. Myers, "Handling Missing Data in Clinical Trials: An Overview," Drug Information Journal, vol. 34, 2000, pp. 525-533.

[3] S. J. Projan, "Why is big Pharma getting out of antibacterial drug discovery?" Current Opinion in Microbiology, vol. 6, no. 5, 2003, pp. 427-430.

[4] A. Knöpfel, B. Grone, and P. Tabeling, Fundamental Modeling Concepts: Effective Communication of IT Systems. John Wiley & Sons, 2006.

[5] M. M. Oken et al., "Toxicity and Response Criteria of the Eastern Cooperative Oncology Group," American Journal of Clinical Oncology, vol. 5, no. 6, December 1982, pp. 649-655.

[6] M. van Eijken et al., "Interventions to Improve Medication Compliance in Older Patients Living in the Community," Drugs & Aging, vol. 20, no. 3, 2003, pp. 229-240.

[7] S. Deterding, D. Dixon, R. Khaled, and L. Nacke, "From game design elements to gamefulness: Defining "gamification"," in Proceedings of the 15th International Academic MindTrek Conference: Envisioning Future Media Environments, ser. MindTrek '11. New York, N.Y., USA: ACM, 2011, pp. 9-15.

[8] K. A. Robinson, C. R. Dennison, D. M. Wayman, D. J. Pronovost, and D. M. Needham, "Systematic Review Identifies Number of Strategies Important for Retaining Study Participants." Journal of Clinical Epidemiology, vol. 60, no. 8, 2007, pp. 757-765.

[9] J. R. Evans and A. Mathur, "The value of Online Surveys," Internet Research, vol. 15, no. 2, 2005, pp. 195-219.

[10] R. Kohavi, R. Longbotham, D. Sommerfield, and R. Henne, "Controlled Experiments on the Web: Survey and Practical Guide," Data Mining and Knowledge Discovery, vol. 18, no. 1, February 2009, pp. 140-181.

[11] D. F. Ferraiolo and D. R. Kuhn, "Role-Based Access Control," in Proceedings of the 15th NIST National Computer Security Conference, 1992, pp. 554-563.

[12] D. Hardt, "RFC6749: The OAuth 2.0 Authorization Framework," http://tools.ietf.org/html/rfc6749/(last accessed: Mar. 25, 2015), October 2012.

[13] D. Cooper, S. Santesson, S. Farrell, S. Boeyen, R. Housley, and W. Polk, "Internet X.509 Public Key Infrastructure Certificate and Certificate Revocation List (CRL) Profile," http://tools.ietf.org/html/rfc5280 (last accessed: Mar. 25, 2015), May 2008.

[14] Health Level 7 International, "FHIR Documentation Index," http://www.hl7.org/implement/standards/fhir/documentation.html (last accessed: Mar. 25, 2015), September 2014.

[15] Object Modeling Group, "Omg unified modeling language, superstructure, v2.1.2," http://www.omg.org/spec/UML/2.1.2/Superstructure/PDF (last accessed: Mar. 25, 2015), November 2007.

[16] The White House, "Blue Button," http://www.whitehouse.gov/open/innovations/BlueButton (last accessed: Mar. 25, 2015).

[17] Federal Institute for Drugs and Medical Devices, "Risk information," http://www.bfarm.de/EN/Drugs/vigilance/InformationRisks/_node.html (last accessed: Mar. 25, 2015).

[18] U.S. Food and Drug Administration, "MedWatch: The FDA Safety Information and Adverse Event Reporting Program," http://www.fda.gov/Safety/MedWatch/default.htm (last accessed: Mar. 25, 2015), February 2015.

[19] R. Steinbrook, "Personally Controlled Online Health Data: The Next Big Thing in Medical Care?" N Engl J Med, vol. 358, no. 16, April 2008, pp. 1653-1656.

[20] Apple, "Apple—Research Kit," https://www.apple.com/researchkit/ (last accessed: Mar. 25, 2015), March 2015.

The invention claimed is:

1. A system for use in course of a clinical trial, said system comprising
   a software platform configured to allow users to create individual data in form of a user profile and to allow two or more users of which at least one is a patient participating in the clinical trial and one is an investigator of the clinical trial to communicate with each other,
   at least one empowerment application (app), configured to build on services and/or functions of the software platform comprising:
   three or more core modules including:
      (i) a personal health record (PHR) module adapted to acquire user data in form of individual healthcare data and store it in a central database, and
      (ii) a data import module comprising a translation repository adapted to import user data in form of individual healthcare data of the at least one patient from a partner application into the central database,
      (iii) a location-based services module, at least one data exploration and analytics app comprising:
   a module which allows real-time exploration and analysis of the individual healthcare data stored in the central database of the software platform accessible by the at least one patient participating in the clinical trial and at least one investigator of the clinical trial, wherein the module detects patterns in the healthcare data stored and/or identities correlations between attributes acquired from the at least one patient furthering an improved quality of life of the at least one patient,
   a storage unit configured to store application data and the user data, a processor configured to
      (i) access the storage unit and analyse the application data and/or user data,
      (ii) form a longitudinal database from the application data and/or user data, wherein the processor causes the system to at least:
   de-identify the at least one patient participating in the clinical trial resulting in de-identification of the at least one patient while communicating during the clinical trial with parties to the clinical trial including the investigator,
   acquire metrics from the at least one patient participating in the clinical trial, wherein the metrics include personal performance metrics and/or medication adherence and compliance metrics during the patient's participation in the clinical trial,
   document the acquired metrics as data points of the at least one patient in the longitudinal database,
   convert the data points in the longitudinal database to longitudinal data which is documented in the user profile of the at least one patient accessible by the investigator of the clinical trial,
   store of all individual healthcare data of the at least one patient in the centralized database and transform the individual healthcare data into a homogenous data format of the software platform,
   provide two or more automated services to at least the at least one patient participating in the clinical trial, wherein one of the two or more automated services include at least reminder services based on the longitudinal data,
   filter and rank data results from the core modules accordingly to a specified location and/or the at least one patient's current location with the location-based services module, and
   make individual data stored on the platform accessible in real-time for exploration and analytics by the users including the at least one patient participating in the clinical trial and the investigator of the clinical trial.

2. The system according to claim 1, wherein further users interacting with the software platform are selected from the group consisting of one or more patient advocacy group members, one or more investigators, one or more physicians, one or more sponsors and/or their representatives, one or more preferred Clinical Research Associates (CRAs), one or more researchers and combinations thereof.

3. The system according to claim 1, wherein data entries of the individual healthcare data comprise a timestamp and a set of attributes and values prior to being stored.

4. The system according to claim 1, wherein the core modules further comprise one or more of the following core modules: messaging module, newsletter module, search module, blogging and discussion forums module, calendar module, notes module, application store and ecosystem module, and/or rating module.

5. The system according to claim 1, wherein the data exploration and analytics module is configured for flexible selection and filtering of specific subsets of data to meet user requirements and a combination across a variety of available data sources.

6. The system according to claim 1, wherein the empowerment app includes an opt-in app, and a data return app, and optionally a data sharing app, data donation app, personal message inbox app, tasks app, medication history app, pharmaceuticals and medication alerts app, investigators and doctors app, community and social network app, disease and treatment knowledge base app and/or a personal performance dashboard app.

7. The system according to claim 6, wherein a data return process of the data return app comprises a sponsor being able to provide a Case Report Form (CRF) data, a Clinical Study Report (CSR), a lay summary, patient- specific summary, user-specific trial data, and to inform the patients and the investigators on its availability via the system being able to view and download the returned data via the system.

8. The system according to claim 6, wherein an opt-in process involves the at least one patient, the one or more investigators and one or more clinical research associates, and wherein the processor, via the opt-in app causes the system to at least:
maintain the de-identification for the at least one patient when providing their consent, and/or refer to terms of use or of participation in a clinical trial.

9. The system according to claim 1, further comprising a data sharing app and wherein the processor, via the data-sharing app causes the system to at least:
create data sets by bundling data items from personal health care data of the at least one patient for sharing data with selected users or user groups,
create a unique identifier, and
to be accessible by the users or user groups with appropriate privileges only while access privileges granted.

10. The system according to claim 1, further comprising an application with game playing elements and activities to trial-related activities.

11. The system according to claim 1, wherein the software platform forms a longitudinal database of self-reported outcomes, preferred medication intakes and/or possible side effects and is adapted to combine data relating to latest information about user's current medication, user's medication history, related information, documented side effects and/or intake plans with surveys and/or documentation of self-reported outcomes provided by the patients.

12. The system according to claim 1, wherein patient empowerment metrics are used for measurement and/or evaluation of patient's empowerment on the platform, during patient's participation in clinical programs, trials, and/or activities.

13. The system according to claim 1, wherein at least two patient empowerment metrics are selected from the group consisting of personal performance, quality of life, social interactions, disease, program knowledge, customer experience, medication adherence and compliance.

14. The system according to claim 1, wherein a bi-directional communication between industry and the at least one patient is enabled during and after a clinical trial, and the system is configured to preserve anonymity of the users.

15. The system according to claim 1, wherein the software platform is configure to implement access rights management using Rule—(RuBAC) and Role-Based Access Control (RBAC) and Single-Sign On (SSO) functionality and techniques for authentication.

16. A computer implemented method for use in course of a clinical trial comprising:
acquiring metrics including personal performance metrics and/or
medication adherence and compliance metrics of at least one patient participating in the clinical trial and documenting the metrics as data points in a longitudinal database accessible by users, wherein the users are parties to the clinical trial,
accessing a partner application and importing individual healthcare data of the at least one patient participating in the clinical trial from a partner application,
storing the individual healthcare data in a standardized data format in the longitudinal database,
de-identify the at least one patient resulting in de-identification of the at least one patient while communicating during the clinical trial with the parties to the clinical trial,
wherein the users comprise at least the a.t least one patient and an investigator of the clinical trial, wherein the users communicate with each other, and wherein the partner application detects patterns in the healthcare data stored and/or identifies correlations between attributes acquired from the at least one patient furthering an improved quality of life of the at least one patient,
providing two or more automated services to the patient, wherein one of the two or more automated services include at least reminder services based on the longitudinal data, and one or more further services selected from the group consisting of retention services, rewards and incentive service, patient education service, medication adherence and compliance service, self-reported outcomes, surveys and questionnaires service, community and social network service, campaign service, A/B testing and combinations thereof, and
filtering and ranking data results obtained from the two or more core modules and/or the two or more automated services accordingly to the specified location and/or current location of the patient.

17. The method of claim 16, wherein access to the longitudinal database is managed via Rule—and Role-Based Access Control and Single-Sign On (SSO) functionality and techniques for authentication.

18. The method of claim 16, wherein the users further comprise one or more sponsors and the sponsors provide returned data in for of a Case Report Form (CRF) data, a Clinical Study Report (CSR), a lay summary, patient-specific summary and/or user-specific trial data.

19. The method of claim 17, wherein the users further comprise one or more sponsors and the sponsors provide returned data in for of a Case Report Form (CRF) data, a Clinical Study Report (CSR), a lay summary, patient-specific summary and/or user-specific trial data.

20. The method of claim 16, wherein information about the at least one patient's current medication, medication history, documented side effects and/or intake plans is combined with surveys and/or documentation of self-reported outcomes provided by patients participating in the clinical trial to form a further longitudinal database of self-reported outcomes, preferred medication intakes and/or possible side effects enabling the investigator to identify the correlations and/or verify research hypotheses.

* * * * *